US012390783B2

(12) United States Patent
Akeroyd et al.

(10) Patent No.: US 12,390,783 B2
(45) Date of Patent: *Aug. 19, 2025

(54) PROTEIN MICROCAPSULES AND METHOD OF PREPARING THE SAME

(71) Applicant: International Flavors & Fragrances Inc., New York, NY (US)

(72) Inventors: Niels Akeroyd, Hilversum (NL); Jeroen van Holland, Hilversum (NL); Volkert de Villeneuve, Hilversum (NL); Robert Allan Hunter, Hilversum (NL); Ronald Gabbard, Union Beach, NJ (US); Yabin Lei, Union Beach, NJ (US); Lewis Michael Popplewell, Union Beach, NJ (US); Takashi Sasaki, Union Beach, NJ (US); Julie Ann Wieland, Union Beach, NJ (US)

(73) Assignee: International Flavors & Fragrances Inc., New York, NY (US)

(*) Notice: Subject to any disclaimer, the term of this patent is extended or adjusted under 35 U.S.C. 154(b) by 687 days.

This patent is subject to a terminal disclaimer.

(21) Appl. No.: 17/416,099

(22) PCT Filed: Dec. 17, 2019

(86) PCT No.: PCT/US2019/066863
§ 371 (c)(1),
(2) Date: Jun. 18, 2021

(87) PCT Pub. No.: WO2020/131879
PCT Pub. Date: Jun. 25, 2020

(65) Prior Publication Data
US 2022/0250025 A1  Aug. 11, 2022

(51) Int. Cl.
| | |
|---|---|
| *B01J 13/16* | (2006.01) |
| *A61K 8/64* | (2006.01) |
| *A61Q 5/00* | (2006.01) |
| *A61Q 5/02* | (2006.01) |
| *A61Q 15/00* | (2006.01) |
| *C11D 3/00* | (2006.01) |
| *C11D 3/20* | (2006.01) |
| *C11D 3/22* | (2006.01) |
| *C11D 3/37* | (2006.01) |
| *C11D 3/382* | (2006.01) |
| *C11D 3/384* | (2006.01) |
| *C11D 3/50* | (2006.01) |

(52) U.S. Cl.
CPC .............. *B01J 13/16* (2013.01); *A61K 8/645* (2013.01); *C11D 3/001* (2013.01); *C11D 3/2072* (2013.01); *C11D 3/222* (2013.01); *C11D 3/3719* (2013.01); *C11D 3/3769* (2013.01); *C11D 3/382* (2013.01); *C11D 3/384* (2013.01); *C11D 3/505* (2013.01); *A61Q 5/00* (2013.01); *A61Q 5/02* (2013.01); *A61Q 15/00* (2013.01)

(58) Field of Classification Search
CPC .......... B01J 13/16; A61K 8/645; C11D 3/001; C11D 3/2072; C11D 3/222; C11D 3/3719; C11D 3/3769; C11D 3/382; C11D 3/384; C11D 3/505; A61Q 5/00; A61Q 5/02; A61Q 15/00
See application file for complete search history.

(56) References Cited

U.S. PATENT DOCUMENTS

| 4,353,809 | A | * | 10/1982 | Hoshi ..................... B01J 13/16 |
|---|---|---|---|---|
| | | | | 428/914 |
| 4,780,321 | A | | 10/1988 | Levy et al. |
| 4,946,624 | A | | 8/1990 | Michael |
| 5,120,475 | A | | 6/1992 | Chen et al. |
| 5,225,118 | A | | 7/1993 | Juang et al. |
| 6,045,835 | A | | 4/2000 | Soper et al. |
| 8,067,028 | B2 | | 11/2011 | Bennett |
| 8,449,918 | B2 | | 5/2013 | Lapidot et al. |
| 9,532,933 | B2 | | 1/2017 | Lei et al. |
| 11,129,778 | B2 | | 9/2021 | Sasaki et al. |
| 11,160,761 | B2 | | 11/2021 | Brahms et al. |
| 2005/0106296 | A1 | * | 5/2005 | Merrill .................. A23L 29/045 |
| | | | | 426/302 |
| 2007/0207174 | A1 | * | 9/2007 | Pluyter .................... A61Q 5/02 |
| | | | | 424/401 |
| 2008/0051490 | A1 | | 2/2008 | Williams et al. |
| 2010/0119679 | A1 | | 5/2010 | Dihora et al. |

(Continued)

FOREIGN PATENT DOCUMENTS

| EP | 2934464 B1 | 2/2018 |
|---|---|---|
| WO | 2007137441 A1 | 12/2007 |

(Continued)

OTHER PUBLICATIONS

International Preliminary Report on Patentability in PCT/US2019/066863, dated Jun. 16, 2021.

(Continued)

*Primary Examiner* — Doan T Phan

(57) ABSTRACT

Microcapsule compositions as disclosed comprising a microcapsule dispersed in an aqueous phase. The microcapsule has a microcapsule core and a microcapsule wall encapsulating the microcapsule core. The microcapsule core contains an active material. The microcapsule wall is formed of a polymeric network comprising a first moiety derived from a protein, and a second moiety derived from a multifunctional electrophile. Also disclosed are preparation methods and consumer products containing the microcapsule compositions.

13 Claims, No Drawings

(56) References Cited

U.S. PATENT DOCUMENTS

| | | |
|---|---|---|
| 2011/0245141 A1 | 10/2011 | Gizaw et al. |
| 2012/0148644 A1 | 6/2012 | Popplewell et al. |
| 2012/0237578 A1 | 9/2012 | Lei et al. |
| 2013/0337023 A1 | 12/2013 | Lei et al. |
| 2014/0023688 A1 | 1/2014 | Bodijono et al. |
| 2014/0106032 A1 | 4/2014 | Dardelle et al. |
| 2014/0363497 A1 | 12/2014 | Sengupta et al. |
| 2015/0164117 A1 | 6/2015 | Kaplan et al. |
| 2015/0250689 A1 | 9/2015 | Dardelle et al. |
| 2015/0252312 A1 | 9/2015 | De Villeneuve et al. |
| 2016/0158121 A1 | 6/2016 | Lei et al. |
| 2016/0193122 A1 | 7/2016 | Lei et al. |
| 2017/0189283 A1 | 7/2017 | Sasaki et al. |
| 2017/0216166 A1 | 8/2017 | Sasaki et al. |
| 2017/0360676 A1 | 12/2017 | Dihora et al. |
| 2017/0367373 A1 * | 12/2017 | Bleiel .................. A23J 3/26 |
| 2018/0015009 A1 | 1/2018 | Soubiran et al. |
| 2018/0064615 A1 | 3/2018 | Brahms et al. |
| 2018/0078468 A1 | 3/2018 | Jerri et al. |
| 2018/0250204 A1 | 9/2018 | Sasaki et al. |
| 2018/0353399 A1 | 12/2018 | Lei et al. |
| 2019/0270064 A1 | 9/2019 | Postma et al. |
| 2020/0046616 A1 | 2/2020 | Lei et al. |
| 2020/0170895 A1 | 6/2020 | Lei et al. |

FOREIGN PATENT DOCUMENTS

| | | | |
|---|---|---|---|
| WO | 2012001604 A2 | 1/2012 | |
| WO | 2012107323 A1 | 8/2012 | |
| WO | 2013059167 A2 | 4/2013 | |
| WO | 2014044840 A1 | 3/2014 | |
| WO | 2015023961 A1 | 2/2015 | |
| WO | 2015126847 A1 | 8/2015 | |
| WO | 2016058909 A1 | 4/2016 | |
| WO | 2018002214 A1 | 1/2018 | |
| WO | WO-2018006089 A1 * | 1/2018 | ............... A61K 8/11 |
| WO | 2018019894 A1 | 2/2018 | |
| WO | 2018077578 A1 | 5/2018 | |
| WO | 2019243425 A1 | 12/2019 | |
| WO | 2019243426 A1 | 12/2019 | |
| WO | 2020195132 A1 | 10/2020 | |
| WO | 2020209907 A1 | 10/2020 | |
| WO | 2020209908 A1 | 10/2020 | |
| WO | 2020209909 A1 | 10/2020 | |

OTHER PUBLICATIONS

International Search Report and Written Opinion in PCT/US2019/066863, dated Jun. 15, 2020.

Office Communication dated May 28, 2020 from U.S. Appl. No. 16/592,033, filed Oct. 3, 2019.

Office Communication dated Nov. 10, 2020 from US. Appl. No. 16/592,033, filed Oct. 3, 2019.

Office Communication dated Aug. 5, 2021 from U.S. Appl. No. 16/592,033, filed Oct. 3, 2019.

Office Communication dated Nov. 23, 2021 from US. Appl. No. 16/592,033, filed Oct. 3, 2019.

Office Communication dated Nov. 24, 2020 in US. Appl. No. 16/780,158, filed Feb. 3, 2020

Office Communication dated Jul. 14, 2021 in US. Appl. No. 16/780,158, filed Feb. 3, 2020

Office Communication dated Feb. 17, 2022 in U.S. Appl. No. 16/780, 158, filed Feb. 3, 2020.

Office Communication dated Feb. 26, 2021 from US. Appl. No. 16/086,198, filed Sep. 18, 2018.

Nesterenko et al. (2013) "Vegetable proteins in microencapsulation: A review of recent interventions and their effectiveness," Industrial Crops and Products 42:469-479.

Nesterenko et al. (2014) "Comparative study of encapsulation of vitamins with native and modified soy protein," Food Hydrocolloids 38:172-179.

* cited by examiner

PROTEIN MICROCAPSULES AND METHOD OF PREPARING THE SAME

CROSS-REFERENCE TO RELATED APPLICATIONS

This application is the national phase under 35 U.S.C. § 371 of PCT International Application No. PCT/US2019/066863, filed Dec. 17, 2019, which claims priority to U.S. Application Ser. No. 62/834,373 filed Apr. 15, 2019. The contents of all applications are incorporated by reference in their entirety.

BACKGROUND

Microcapsules are used in various consumer products in which there is a need to deliver, apply, or release an active material including a fragrance, flavor, and malodor counteraction agent to a target area in a time-delayed or controlled manner.

Conventional microcapsules typically have a microcapsule wall formed of a synthetic polymer such as a melamine formaldehyde polymer, a polyurea, or a polyacrylate. Consumers prefer environment friendly, natural materials over synthetic polymers and demand development of green, sustainable products and technologies.

Microcapsules prepared from natural materials have been reported in Mint et al., WO 2016/185171 A1, with a fungal chitosan. Silk fibroin particles have been found suitable to encapsulate fragrance oil. See Kaplan et al., US 2015/0164117 A1. Biomolecules have been used as emulsifiers in microcapsule preparation. See WO 2016/193435 A1, WO 2017/102812 A1, US 2018/0078468 A1, WO 2018/019894 A1, WO 2018/019896 A1, and WO 2017/102812 A1. Multilayered coacervate capsules are typically conventional microcapsules coated with the coacervate between gelatin and gum arabic. See U.S. Pat. No. 4,946,624, WO 2012/001604 A1, US 2015/0250689 A1 and WO 2018/002214 A1. Chitosan and other biomolecules have also been explored and used to prepare microcapsule compositions. See WO 2015/023961 A1, WO 2018/077578 A1 and EP 2 934 464 B1. Proteins have been used to coat microcapsules to improve deposition. See US 2017/0189283 A1.

US 2017/0360676 A1 describes a polysaccharide delivery particle that is environmentally biodegradable.

However, none of these microcapsules and particles demonstrates both high performance and environmentally degradability that meet the customers' demand.

There is a need to develop environment friendly microcapsules with a high fragrance performance for use in laundry, washing, cleaning, surface care, and personal and skin care.

SUMMARY OF THE INVENTION

This invention is based on the discovery that certain microcapsule compositions possess unexpected high perceived olfactory intensity, great stability, and friendly to the environment.

Accordingly, one aspect of this invention relates to a process of preparing a microcapsule composition comprising the step of: (i) providing an oil-in-water emulsion having a plurality of oil droplets dispersed in an aqueous phase, in which the oil-in-water emulsion contains a polyisocyanate, the oil phase contains an active material, and the aqueous phase contains a protein, (ii) providing a condition sufficient to induce interfacial polymerization in the oil-in-water emulsion to form a microcapsule slurry that contains microcapsules each having a microcapsule wall encapsulating a microcapsule core, thereby obtaining the microcapsule composition, provided that no substantial amount of a polyamine other than the protein is added at any stage of the process. Each oil droplet can have a size of 0.1 µm to 100 µm in diameter and each microcapsule has a size of 0.2 µm to 100 µm in diameter. The process can further include the step of (iii) curing the microcapsule at a temperature of 0° C. to 125° C. for 10 minutes to 24 hours and (iv) after the curing step, adding a chitosan aqueous solution to 0.5% to 5% by weight of the microcapsule composition at a pH of 1 to 5, and heating the resultant mixture to 35° C. to 95° C. (e.g., 45° C. to 75° C., for 10 minutes to 10 hours).

In one embodiment, the polyisocyanate is present in each oil droplet or aqueous phase at a level 0.2% to 5% (e.g., 0.2% to 3%, 0.2% to 2% and 0.3% to 1.5%), the protein is present at a level of 0.8% to 15% (e.g., 0.8% to 10% and 1% to 5%), all by weight of the microcapsule composition, and the weight ratio of the protein and the polyisocyanate is 1:1 to 10:1. Preferably, the protein is a pea protein, either native or denatured.

Examples of the polyisocyanate include a trimer of hexamethylene diisocyanate, a trimer of isophorone diisocyanate, a biuret of hexamethylene diisocyanate, a polyisocyanurate of toluene diisocyanate, a trimethylol propane-adduct of toluene diisocyanate, a trimethylol propane-adduct of xylylene diisocyanate, and combinations thereof.

Exemplary active materials are a fragrance, flavor, malodor counteractive agent, pro-fragrance, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, and combinations thereof. In one embodiment, the active material is a high-performing fragrance.

The process can further comprise a step of (iv) drying the microcapsule slurry to remove water, wherein the drying step is performed by spray drying, filtration, or freeze drying.

The process can also include a step of adding a deposition polymer to the microcapsule slurry, wherein the deposition polymer is selected from the group consisting of trimonium, methacrylamidopropyl trimethyl ammonium, acrylamidopropyl trimethylammonium, acrylamide, acrylic acid, dimethyl ammonium, xlylose, galactose, hydroxypropylated glucose, hydroxyethylated glucose, hydroxymethylated glucose, vinylamine, ethylenimine, functionalized branched polyethylenimine, vinylformamide, vinylpyrollidone, caprolactone, catechol, vinylalcohol, chitosan, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-79 and hydrolyzed keratin co-polymer, polyquaternium-80, polyquaternium-81, polyquaternium-82, polyquaternium-86, polyquaternium-88, polyquaternium- 101, polyvinylamine, polyethyleneimine, a copolymer of vinylamine and vinylformamide, a copolymer of acrylamide and 3-methacryloylaminopropyl trimethylammonium, a 3-acrylamidopropyl trimethylammonium polymer or its copolymer, a diallyldimethyl-ammoniumchloride polymer and its copolymer, a polysaccharide with saccharide unit functionalized with hydroxypropyl trimmonium, ethyltrimonium chloride methacrylate/hydrolyzed wheat protein copolymer, alkyl-monium hydroxypropyl hydrolyzed protein, and combinations thereof.

The process can also include the step of adding a polyphenol (e.g., a tannic acid) to the oil-in-water emulsion at a level of 0.1% to 2.5% by weight of the microcapsule composition.

The microcapsule thus prepared typically contains 10% to 90% of the fragrance, 1% to 20% of a moiety derived from the protein, and 0.2% to 6% of a moiety derived from the polyisocyanate, all by weight of the microcapsule.

Also within the scope of this invention are microcapsule compositions. The microcapsule compositions each have one or more microcapsules dispersed in an aqueous phase, wherein the microcapsule has a microcapsule core and a microcapsule wall encapsulating the microcapsule core. In some embodiments, the microcapsule compositions are prepared by the process described above. In other embodiments, the microcapsule compositions are prepared by other processes including conventional interfacial polymerization and 3D printing. Both the microcapsule shell and microcapsule core can be printed using a printing system. See WO2016172699A1. The printing steps generally include depositing the active materials and the microcapsule shell material in a layer-by-layer fashion, preferably through separate printer heads. The microcapsule shell material can be polymers containing a first moiety derived from a protein and a second moiety derived from a multi-functional electrophile such as a polyisocyanate.

The microcapsule core contains an active material, Suitable active materials for printing include fragrances, flavors, malodor counteractive agents, cosmetic actives, and nutrients. the active material is selected from the group consisting of a fragrance, flavor, cosmetic active, malodor counteractant, pro-fragrance, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, nutrient, and combinations thereof.

The first moiety derived from the protein is present at a level of 0.2% to 10% by weight of the microcapsule composition and is selected from the group consisting of pea proteins, potato proteins, brown rice proteins, white rice proteins, wheat proteins, egg proteins, barley proteins, pumpkin seed proteins, oat proteins, almond proteins, whey proteins, and combinations thereof.

The second moiety derived from the multi-functional electrophile is present at a level of 0.1% to 10% by weight of the microcapsule composition. Optionally, the microcapsule composition has 0.1% to 10% of a third moiety derived from a polyphenol.

Still within the scope of this invention is a consumer product containing a microcapsule composition of this invention. The consumer product can be a baby care product, a diaper rash cream or balm, a baby powder, a diaper, a bib, a baby wipe, a cosmetic preparation, a powder foundation, a liquid foundation, an eye shadow, a lipstick or lip balm, a home care product, an all-purpose cleaner, a scent drop product, a bathroom cleaner, a floor cleaner, a window cleaner, a plastics polish, a bleach, a toilet cleaner, a toilet rimblock, a bath tissue, a paper towel, a disposable wipe, liquid air freshener, air freshener spray, a spray dispenser product, an incense stick, a rug deodorizer, a candle, a room deodorizer, a liquid dish detergent, an automatic dish detergent, a powder dish detergent, a leather detergent, a tablet dish detergent, a paste dish detergent, a unit dose tablet or capsule, a flavor, a beverage flavor, a diary flavor, a fruit flavor, a miscellaneous flavor, a sweet goods flavor, a tobacco flavor, a toothpaste flavor, a chewing gum, a breath freshener, an orally dissolvable strips, a chewable candy, a hard candy, an oral care product, a tooth paste, a toothbrush, a dental floss, an oral rinse, an tooth whitener, a denture adhesive, a health care device, a tampon, a feminine napkin, an anti-inflammatory balm, an anti-inflammatory ointment, an anti-inflammatory spray, a disinfectant, a personal care product, a soap, a bar soap, a liquid soap, a bath fragrance, a body wash, a non-aerosol body spray, a body milk, a cleanser, a body cream, a hand sanitizer, a hand wash, a functional product base, a sunscreen lotion, a sunscreen spray, a deodorant, an anti-perspirant, an roll-on product, an aerosol product, a natural spray product, a wax-based deodorant, a glycol type deodorant, a soap type deodorant, a facial lotion, a body lotion, a hand lotion, a miscellaneous lotion, a body powder, a shave cream, a shave gel, a shave butter, a bath soak, a shower gel, an exfoliating scrub, a foot cream, a facial tissue, a cleansing wipe, a talc product, a hair care product, a hair care with ammonia, a shampoo, a hair conditioner, a hair rinse, a hair refresher, a hair fixative or styling aid, a hair bleach, a hair dye or colorant, a fabric care product, a fabric softener, a liquid fabric softener, a fabric softener sheet, a drier sheet, a fabric refresher, an ironing water, a detergent, a laundry detergent, a liquid laundry detergent, a powder laundry detergent, a tablet laundry detergent, a laundry detergent bar, a laundry detergent cream, a hand wash laundry detergent, a scent booster, a fragrance, a cologne, compounds, an encapsulated fragrance, a fine fragrance, a men's fine fragrance, a women's fine fragrance, a perfume, a solid perfume, an Eau De Toilette product, a natural spray product, a perfume spray product, an insect repellent product, and a wildlife scent.

The details of one or more embodiments of the invention are set forth in the description below. Other features, objects, and advantages of the invention will be apparent from the description and the claims.

DETAILED DESCRIPTION OF THE INVENTION

It has been found that certain protein microcapsules have unexpectedly high fragrance performance and are environment friendly. These protein microcapsule compositions have been successfully incorporated into many consumer applications.

In one embodiment, the microcapsule compositions of this invention can be prepared following the steps of: (i) providing an oil-in-water emulsion having a plurality of oil droplets dispersed in an aqueous phase, in which the oil-in-water emulsion contains a polyisocyanate, the oil phase contains an active material, and the aqueous phase contains a protein, (ii) providing a condition sufficient to induce interfacial polymerization in the oil-in-water emulsion to form a microcapsule slurry that contains microcapsules each having a microcapsule wall encapsulating a microcapsule core, thereby obtaining the microcapsule composition, provided that no substantial amount of an emulsifier other than the protein is added at any stage of the process. Further in some embodiments, no substantial amount of a polyamine other than the protein is added at any stage of the process.

The interfacial polymerization can be induced by heating the oil-in-water emulsion to an elevated temperature (e.g., at least 35° C., at least 45° C., at least 55° C., and 35° C. to 95° C.). It can also be induced by adding to the oil-in-water emulsion a catalyst such as 1,4-diazabicyclo-[2.2.2]octane (i.e., DABCO).

Optionally, the preparation process further comprises the step of: (iv) curing the microcapsule slurry at a temperature of 0° C. to 125° C. (e.g., 15° C. to 110° C., 25° C. to 100° C., 45° C. to 95° C., and 50° C. to 90° C.) for 10 minutes to 48 hours (e.g., 15 minutes to 24 hours, 30 minutes to 10 hours, and 30 minutes to 6 hours).

The oil-in-water emulsion can be prepared using conventional emulsion techniques by emulsifying an oil phase into an aqueous phase without an additional capsule formation aid. The protein can act both as an emulsifier and a cross-linking agent. In one embodiment, the oil phase contains the active material (such as a fragrance), the polyisocyanate and a core solvent (such as caprylic/capric triglyceride). The aqueous phase contains water and the protein without an additional emulsifier. In another embodiment, the oil phase contains the active material and a core solvent. The aqueous phase contains water, the polyisocyanate, and the protein. In still another embodiment, the polyisocyanate is to a pre-formed oil-in-water emulsion, not to either the oil or aqueous phase before the formation of the emulsion.

A native protein is preferred. However, in some embodiments, the process includes a step of denaturing the protein by pH adjustment, heat, or adding a chaotropic agent to the oil-in-water emulsion or to the protein before adding to the oil-in-water emulsion.

The microcapsule composition thus prepared typically have a pH of 3 to 12, preferably 3 to 10 and more preferably 4 to 9 (e.g., 5 and 9).

The microcapsules of this invention each have a core-shell structure with a single microcapsule core and a single microcapsule wall encapsulating the single microcapsule core. The microcapsule wall has an inner surface and outer surface. The inner surface is in contact with the microcapsule core. The outer surface is in contact with the environment where the microcapsule resides, e.g., a water phase, skin, and hair.

The microcapsule wall is formed of a polymeric network containing at least two different moieties: (i) the first moiety derived from a protein, (ii) the second moiety derived from a polyisocyanate, and (iii) optionally a third moiety derived from a polyphenol.

Not to be bound by any theory, it is believed that the amino groups (—$NH_2$) on the protein crosslink with the isocyanate groups (—NCO) on the polyisocyanate to form urea bonds (—NHCONH—, a covalent bond), and the hydroxyl groups (—OH) on the polyphenol crosslink with the isocyanate groups on the polyisocyanate to form urethane bonds (—OCONH—). After the crosslinking reactions, in the polymeric network, the protein converts to the first moiety, the polyisocyanate turns into the second moiety in which the isocyanate groups transform to be a part of the urea bonds, and the polyphenol becomes the third moiety in which the hydroxyl groups transform to be a part of the urethane bonds.

The microcapsule thus prepared has a particle size (in diameter) of 0.1 microns to 1000 microns (e.g., 0.5 microns to 500 microns, 1 micron to 200 microns, and 1 micron to 100 microns) with a lower limit of 0.1 microns, 0.5 microns, 1 micron, 2 microns, or 5 microns and an upper limit of 1000 microns, 500 microns, 200 microns, 100 microns, 75 microns, 50 microns, or 30 microns. Preferably, the microcapsule has a particle size of 20 microns to 200 microns.

The microcapsules can be positively or negatively charged with a zeta potential of −200 mV to +200 mV (e.g., 10 mV or greater, 25 mV or greater, 40 mV or greater, 25 mV to 200 mV, and 40 mV to 100 mV) with a lower limit of −200 mV, −150 mV, −100 mV, −50 mV, −25 mV, −10 mV, 0 mV, 10 mV, 20 mV, or 40 mV and an upper limit of 200 mV, 150 mV, 100 mV, 50 mV, 40 mV, 20 mV, 10 mV, 0 mV, −10 mV, and −25 mV. Preferably, the microcapsules each are positively charged. Not to be bound by theory, positively charged microcapsules have a strong affinity to specific animate and inanimate surfaces (e.g., hair and fabric), and also are unexpectedly stable in certain consumer product bases such as hair conditioners, shampoos, shower gels, and fabric conditioners.

The microcapsule of this invention is biodegradable and thus environment friendly. "Biodegradable" as used herein with respect to a material, such as a microcapsule as a whole and/or a biopolymer of the microcapsule shell, has no real or perceived health and/or environmental issues, and is capable of undergoing and/or does undergo physical, chemical, thermal, microbial and/or biological degradation. Ideally, a microcapsule and/or biopolymer is deemed "biodegradable" when the microcapsule and/or biopolymer passes one or more of the Organization for Economic Co-operation and Development (OECD) tests including, but not limited to OECD 301/310 (Ready biodegradation), OECD 302 (inherent biodegradation), the International Organization for Standardization (ISO) 17556 (solid stimulation studies), ISO 14851 (fresh water stimulation studies), ISO 18830 (marine sediment stimulation studies), OECD 307 (soil stimulation studies), OECD 308 (sediment stimulation studies), and OECD 309 (water stimulation studies). In particular embodiments, the microcapsules are readily biodegradable as determined using the OECD 310 test. The pass level for ready biodegradability under OECD 310 is 60% of $CO_2$ production is reached within the 60-day period of the test.

Polypeptide Biopolymers and Proteins

Suitable proteins for this invention include a whey protein, a pea protein, a rice protein, a wheat protein (e.g., a concentrate or isolate), an egg protein, and a plant storage protein (e.g., a concentrate or isolate) such as a barley protein, a brown rice protein, a white rice protein, a pumpkin seed protein, an oat protein, a potato protein, almond protein, or any combination thereof.

As is conventional in the art, a "polypeptide" or "protein" is a linear organic polymer composed of amino acid residues bonded together in a chain, forming part of (or the whole of) a protein molecule. "Polypeptide" or "protein" as used herein means a natural polypeptide, polypeptide derivative, and/or modified polypeptide. The polypeptide may exhibit an average molecular weight of from 1,000 Da to 40,000,000 Da and/or greater than 10,000 Da and/or greater than 100,000 Da and/or greater than 1,000,000 Da and/or less than 3,000,000 Da and/or less than 1,000,000 Da and/or less than 500,000 Da, or a range delimited by any one of these molecular weights.

As used herein, "whey protein" refers to the protein contained in whey, a dairy liquid obtained as a supernatant of curds when milk or a dairy liquid containing milk components, is processed into cheese curd to obtain a cheese-making curd as a semisolid. Whey protein is generally understood in principle to include the globular proteins β-lactoglobulin and α-lactalbumin at various ratios such as 1:1 to 5:1 (e.g., 2:1). It may also include lower amounts of serum albumin, immunoglobulin and other globulins. The term "whey protein" is also intended to include partially or completely modified or denatured whey proteins. Purified β-lactoglobulin and/or α-lactalbumin polypeptides may also be used in preparation of microcapsules of this invention.

Plant storage proteins are proteins that accumulate in various plant tissues and function as biological reserves of metal ions and amino acids. Plant storage proteins can be classified into two classes: seed or grain storage proteins and vegetative storage proteins. Seed/grain storage proteins are a set of proteins that accumulate to high levels in seeds/grains during the late stages of seed/grain development, whereas vegetative storage proteins are proteins that accumulate in vegetative tissues such as leaves, stems and, depending on plant species, tubers. During germination, seed/grain storage proteins are degraded and the resulting amino acids are used by the developing seedlings as a nutritional source. In some embodiments, the plant storage protein used in the preparation of a microcapsule of the invention is a seed or grain storage protein, vegetable storage protein, or a combination thereof. In certain embodiments, the seed storage protein is a leguminous storage protein. In particular embodiments, the seed/grain storage protein is extracted from leguminous plants and particularly from soya, lupine, pea, chickpea, alfalfa, horse bean, lentil, and haricot bean; from oilseed plants such as colza, cottonseed and sunflower; from cereals like wheat, maize, barley, malt, oats, rye and rice (e.g., brown rice protein), or a combination thereof. In other embodiments, the plant storage protein is a vegetable protein extracted from potato or sweet potato tubers.

In particular embodiments, the plant storage protein is intended to include a plant protein isolate, plant protein concentrate, or a combination thereof. Plant storage protein isolates and concentrates are generally understood to be composed of several proteins. For example, pea protein isolates and concentrates may include legumin, vicilin and convicilin proteins. Similarly, brown rice protein isolates may include albumin, globulin and glutelin proteins. The term "plant storage protein" is also intended to include a partially or completely modified or denatured plant storage protein. Individual storage polypeptides (e.g., legumin, vicilin, convicilin, albumin, globulin or glutelin) may also be used in preparation of microcapsules of this invention.

"Gelatin" refers to a mixture of proteins produced by partial hydrolysis of collagen extracted from the skin, bones, and connective tissues of animals. Gelatin can be derived from any type of collagen, such as collagen type I, II, III, or IV. Such proteins are characterized by including Gly-Xaa-Yaa triplets wherein Gly is the amino acid glycine and Xaa and Yaa can be the same or different and can be any known amino acid. At least 40% of the amino acids are preferably present in the form of consecutive Gly-Xaa-Yaa triplets.

A whey protein or plant storage protein of this invention may be native, partially or completely denatured by any suitable method, preferably without causing gelation of the whey protein or plant storage protein. The protein is used in the form of protein isolates or concentrates.

Denaturation is a process in which proteins (polypeptides) lose the quaternary structure, tertiary structure, and secondary structure present in their native state, by application of a denaturation condition. During denaturation, proteins change their conformational structure by unfolding, thereby making amine (—NH$_2$) and hydroxyl (—OH) groups available for crosslinking with polyisocyanate to form a microcapsule wall. Denaturation is reversible (the proteins can regain their native state when the denaturing influence is removed) or irreversible.

Exemplary conditions for protein denaturation include, but are not limited to, radiation, exposure to heat or cold, changes in pH with an acid or base, exposure to denaturing agents such as detergents, inorganic salt, organic solvent (e.g., alcohol, ethyl acetate, and chloroform), urea, or other chaotropic agents, or mechanical stress including shear. In certain embodiment, a chaotropic agent with positive chaotropic activity value is used (kJ·kg$^{-1}$ on the Hallsworth Scale).

Exemplary chaotropic agents are guanidine salts (e.g., guanidine hydrochloride and guanidine carbonate), urea, polysorbate, sodium benzoate, vanillin, o-cresol, phenol, propanol, formamide, ethanol, fructose, ammonium sulfate, ammonium chloride, ammonium nitrate, ammonium phosphate, potassium sulfate, potassium chloride, potassium iodide, potassium nitrate, potassium phosphate, sodium sulfate, sodium chloride, sodium bromide, sodium nitrate, sodium phosphate, guanidine thiocyanate, xylose, glycerol, benzyl alcohol, ethyl acetate, triton X-100, ethyl acetate, cetyltrimethylammonium halide, acetone, sodium dodecyl sulfate (SDS), hydrochloric acid, sulfuric acid, polyethylene glycol, glutaraldehyde, and combinations thereof. Any amount of the chaotropic agent can be used.

By way of illustration, when an 8% pea storage protein solution (w/v) is used, the solution may be treated at a temperature of 80-90° C. for 20-30 minutes (or preferably 85° C. for 25 minutes) to yield a denatured pea storage protein. However, it will be appreciated that higher temperatures and shorter times may also be employed. In particular embodiments, the whey protein or plant storage protein is partially or completely denatured with, e.g., guanidine carbonate. Notably, it has been found that the degree and method to denature the protein can have a significant impact on performance. Accordingly, in certain embodiments, the whey protein or plant storage protein is denatured with a chaotropic agent so that 20% to 100% (e.g., at least 20%, at least 40%, at least 60%, at least 90%, 95%, or 99%, w/w) of the whey protein or plant storage protein used in the preparation of the microcapsules is denatured.

The protein used in the microcapsule can also be derivatized or modified (e.g., derivatized or chemically modified). For example, the protein can be modified by covalently attaching sugars, lipids, cofactors, peptides, or other chemical groups including phosphate, acetate, methyl, and other natural or unnatural molecule.

The microcapsule wall contains the protein at a level of 20 wt % to 98 wt % (e.g., 30 wt % to 95 wt %, 35 wt % to 95 wt %, and 65 wt % to 85 wt %) by weight of the microcapsule wall. Microcapsule walls with a high protein content are readily biodegradable and at the same time efficiently encapsulate a fragrance with a satisfactory release profile.

Polyisocyanates

Polyisocyanates each have at least two isocyanate (—NCO) groups reactive towards proteins or polyphenols. The polyisocyanate can be aromatic, aliphatic, linear, branched, or cyclic. It can be water soluble or water dispersible. Alternatively, it is soluble in an organic solvent or fragrance oil. In some embodiments, the polyisocyanate contains, on average, 2 to 4 isocyanate groups. In particular embodiments, the polyisocyanate contains at least three isocyanate functional groups. In certain embodiments, the polyisocyanate is water insoluble.

In particular embodiments, the polyisocyanate used in this invention is an aromatic polyisocyanate. Desirably, the aromatic polyisocyanate includes a phenyl, tolyl, xylyl, naphthyl or diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

One class of suitable aromatic polyisocyanates are those having the generic structure shown below, and its structural isomers

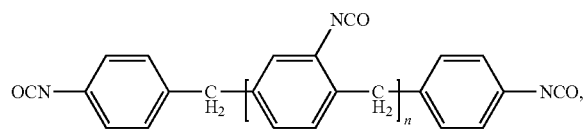

wherein n can vary from zero to a desired number (e.g., 0-50, 0-20, 0-10, and 0-6) depending on the type of cross-linker used. Preferably, the number of n is limited to less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5. Commercially-available polyisocyanates include products under the trade names of LUPRANATE® M20 (chemical name: polymeric methylene diphenyl diisocyanate, i.e., "PMDI"; commercially available from BASF containing isocyanate group "NCO" 31.5 wt %), where the average n is 0.7; PAPI™ 27 (PMDI commercially available from Dow Chemical having an average molecular weight of 340 and containing NCO 31.4 wt %) where the average n is 0.7; MONDUR® MR (PMDI containing NCO at 31 wt % or greater, commercially available from Covestro, Pittsburgh, Pennsylvania) where the average n is 0.8; MONDUR® MR Light (PMDI containing NCO 31.8 wt %, commercially available from Covestro) where the average n is 0.8; MONDUR® 489 (PMDI commercially available from Covestro containing NCO 30-31.4 wt %) where the average n is 1; poly[(phenylisocyanate)-co-formaldehyde] (Aldrich Chemical, Milwaukee, WI), other isocyanate monomers such as DESMODUR® N3200 (poly(hexamethylene diisocyanate) commercially available from Covestro), and Takenate™ D-110N (trimethylol propane-adduct of xylylene diisocyanate, Mitsui Chemicals America, Inc., Rye Brook, NY, containing NCO 11.5 wt %), DESMODUR® L75 (a polyisocyanate base on toluene diisocyanate commercially available from Covestro), and DESMODUR® IL (another polyisocyanate based on toluene diisocyanate commercially available from Covestro).

The structures of certain commercially available polyisocyanates of the invention are shown below:

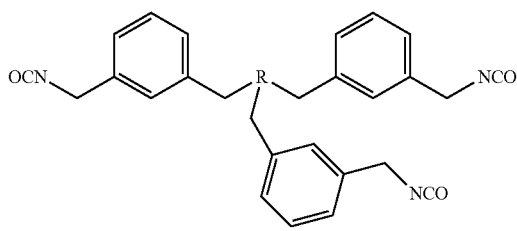

or its structural isomer. R can be a $C_1$-$C_{10}$ alkyl, $C_1$-$C_{10}$ ester, or an isocyanurate. Representative polyisocyanates of this structure are commercially available under the trade names of TAKENATE™ D-110N (Mitsui), DESMODUR® L75 (Covestro), and DESMODUR® IL (Covestro).

Polyisocyanate Takenate™ D-110N and other polyisocyanates are available typically in an ethyl acetate solution. Preferably, ethyl acetate is replaced with a solvent having a high flash point (e.g., at least 100° C., at least 120° C., and at least 150° C.). Suitable solvents include triacetin, triethyl citrate, ethylene glycol diacetate, benzyl benzoate, and combinations thereof.

As an illustration, Takenate™ D-110N (a trimethylol propane-adduct of xylylene diisocyanate solution in ethyl acetate) is combined with benzyl benzoate and vacuum distilled to remove ethyl acetate to obtain a polyisocyanate solution containing 59% of the trimethylol propane-adduct of xylylene diisocyanate solution and 41% of benzyl benzoate. This polyisocyanate solution has a flash point of at least 60° C. This polyisocyanate solution in benzyl benzoate, together with PVP/PQ-11 or Flexan® II/CMC, can be used to prepare the microcapsule compositions.

Other examples of the aromatic polyisocyanate include 1,5-naphthylene diisocyanate, 4,4'-diphenylmethane diisocyanate (MDI), hydrogenated MDI, xylylene diisocyanate (XDI), tetramethylxylol diisocyanate, 4,4'-diphenyldimethylmethane diisocyanate, di- and tetraalkyl-diphenylmethane diisocyanate, 4,4'-dibenzyl diisocyanate, 1,3-phenylene diisocyanate, 1,4-phenylene diisocyanate, the isomers of tolylene diisocyanate (TDI), 4,4'-diisocyanatophenyl-perfluoroethane, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate, and combinations thereof.

In other particular embodiments, the polyisocyanate is an aliphatic polyisocyanate such as a trimer of hexamethylene diisocyanate, a trimer of isophorone diisocyanate, and a biuret of hexamethylene diisocyanate. Exemplary aliphatic polyisocyanates include commercial products, e.g., BAYHYDUR® N302, BAYHYDUR® N303, BAYHYDUR® N304, and BAYHYDUR® N305, which are aliphatic water-dispersible based on hexamethylene diisocyanate; DESMODUR® N3600, DESMODUR® N3700, and DESMODUR® N3900, which are low viscosity, polyfunctional aliphatic polyisocyanates based on hexamethylene diisocyanate; and DESMODUR® 3600 and DESMODUR® N100 which are aliphatic polyisocyanates based on hexamethylene diisocyanate, each of which is available from Covestro, Pittsburgh, PA). More examples include 1-methyl-2,4-diisocyanatocyclohexane, 1,6-diisocyanato-2,2,4-trimethyl-hexane, 1,6-diisocyanato-2,4,4-trimethylhexane, 1-isocyanatomethyl-3-isocyanato-1,5,5-tri-methylcyclohexane, chlorinated and brominated diisocyanates, phosphorus-containing diisocyanates, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, and combinations thereof. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane, dimer fatty acid diisocyanate, and combinations thereof.

The weight average molecular weight of useful polyisocyanates varies from 200 Da to 2500 Da, 250 Da to 1000 Da and preferable from 275 Da to 500 Da.

The range of the polyisocyanate content can vary from 0.5% to 40% (e.g., 1% to 35%, 2% to 30%, and 3% to 25%) by weight of the microcapsule wall.

During the process of preparing the microcapsule composition of this invention, polyisocyanate can be added to the aqueous phase, the oil phase, or the oil-in-water emulsion.

wall materials. More polyisocyanate examples can be found in WO 2004/054362 and WO 2017/192648.

Polyphenols

The microcapsule composition of this invention optionally contain a third moiety derived from a polyphenol especially those having a 3,4,5-trihydroxyphenyl group or 3,4-dihydroxypheny group such as tannic acid, which has a typical chemical structure as follows:

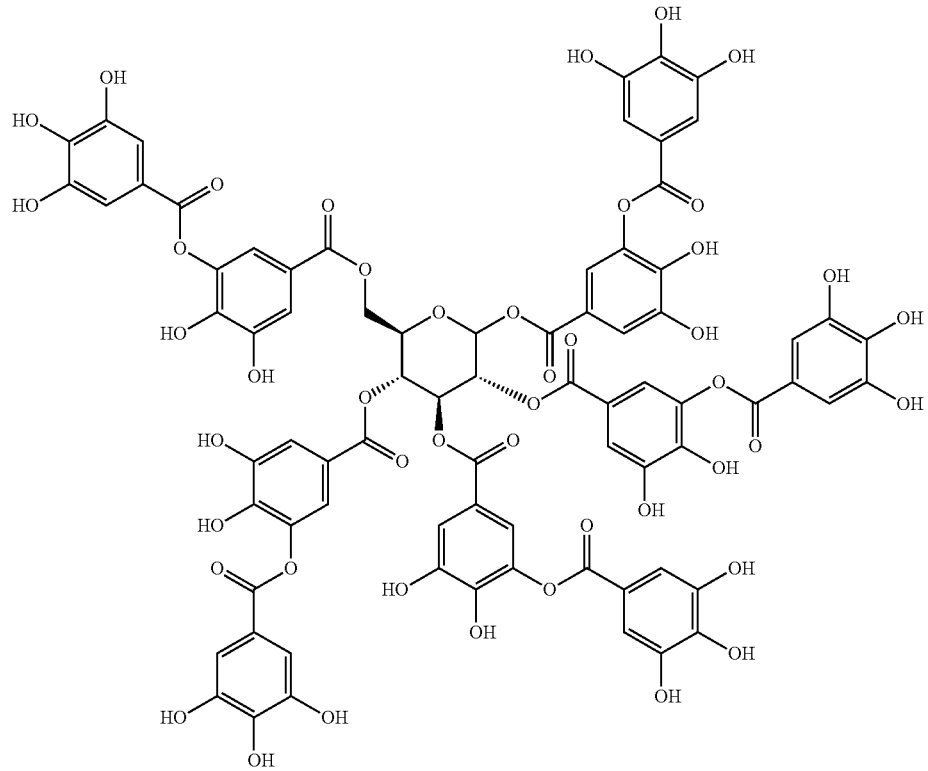

Representative structure of tannic acid

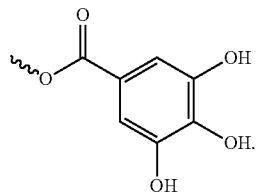

A galloyl moiety

In some embodiments, the polyfunctional isocyanate used in the preparation of the microcapsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the encapsulating polymers as capsule The above chemical formula is often given as $C_{76}H_{52}O_{46}$, which corresponds with decagalloyl glucose. However, commercially available tannic acid typically comprises a mixture of polygalloyl glucoses or polygalloyl quinic acid esters with the number of galloyl moieties per molecule ranging from 2 up to 20 (e.g., 2 to 15 and 2 to 12) and a molecular weight of 400 Daltons to 3500 Daltons (e.g., 496 to 3232 Daltons, 496 Daltons to 2472 Daltons, 180+152n Daltons, and 192+152n Daltons, in which n is between 2 and 13). Tannic acid has a weak acidity (e.g., pKa around 6) with a pH value of 2 to 5 (e.g., 3-4 and 2.5 to 3.5) in an aqueous solution containing 1% of tannic acid. Tannic acid has a water solubility of from 100 g/L to 2850 g/L (e.g., 250 g/L) at 25° C.

Tannic acid is usually extracted from any of the following plant parts: Tara pods (*Caesalpinia spinosa*), gallnuts from *Rhus semialata* or *Quercus infectoria* or Sicilian Sumac leaves (*Rhus coriaria*). Tannic acid is commercially available from suppliers such as Sigma-Aldrich (St Louis) and Ajinomoto OmniChem (Wetteren, Belgium) under the trademarks of Tanal® 01 (polygalloyl glucose, molecular weight 1440 Daltons), Tanal® 02 (polygalloyl glucose, molecular weight 1040 Daltons), and Tanal® 04 (polygalloyl quinic acid ester, molecular weight 860 Daltons).

In additional to polyphenols, other polyols can also be used to prepare the microcapsule compositions of this invention. See polyols described in WO 2015/023961. Examples include pentaerythritol, dipentaerythritol, glycerol, polyglycerol, ethylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, polyphenol, and combinations thereof.

Multi-functional aldehydes such as glutaraldehyde and glyoxal form derivatives such as monohydrates, dehydrates, acetal, or hemiacetal in aqueous solution under certain pH ranges (i.e., in an acidic condition). These multi-functional aldehyde derivatives have hydroxyl (—OH) groups that are reactive toward polyisocyanates to form polyurethane bonds. As such, multi-functional aldehydes act as multi-functional nucleophiles under certain conditions such as at a pH of 3 to 8.

Polyphenols, polyols, and multi-functional aldehydes can be present at a level of 0 to 40% (e.g., 1% to 35%, 5% to 35%, and 10% to 30%) by weight of the microcapsule wall or 0 to 10% (e.g., 0.01% to 8%, 0.02% to 7%, 0.1% to 5%, and 0.2% to 3%) by weight of the microcapsule composition.

Catalysts

In sometime embodiments, a catalyst is added to induce the interfacial polymerization in the formation of a capsule wall. Examples include metal carbonates, metal hydroxide, amino or organometallic compounds and include, for example, sodium carbonate, cesium carbonate, potassium carbonate, lithium hydroxide, 1,4-diazabicyclo[2.2.2]octane (i.e., DABCO), N,N-dimethylaminoethanol, N,N-dimethylcyclohexylamine, bis-(2-dimethylaminoethyl) ether, N,N dimethylacetylamine, stannous octoate, and dibutyltin dilaurate.

Other Encapsulating Polymers

The microcapsule composition of this invention optionally has a second, third, fourth, fifth, or sixth microcapsule each formed of an encapsulating polymer selected from the group consisting of a sol-gel polymer (e.g., silica), polyacrylate, polyacrylamide, poly(acrylate-co-acrylamide), polyurea, polyurethane, starch, gelatin and gum Arabic, poly(melamine-formaldehyde), poly(urea-formaldehyde), and combinations thereof. A branched polyethyleneimine and its derivatives can also be coated onto the microcapsule wall to prepare a microcapsule having a positive zeta potential.

These encapsulating polymers include sol-gel microcapsules, polyacrylate microcapsules, polyacrylamide microcapsules, poly(acrylate-co-acrylamide) microcapsules, aminoplast and gelatin microcapsules, urea-formaldehyde and melamine-formaldehyde microcapsules. See US 2018/0015009 A1. The microcapsule composition of this invention optionally contains one or more additional microcapsules, e.g., a second, third, fourth, fifth, or sixth microcapsules. Each of these microcapsules can be any of the microcapsule described above.

These additional microcapsules can be any microcapsules described above but different from each other in term of microcapsule size, degree of polymerization, degree of crosslinking, encapsulating polymer, thickness of the wall, active material, ratio between the wall material and the active material, rupture force or fracture strength, and the like.

Active Materials

The microcapsule core can include one or more active materials including flavors and/or fragrance ingredients such as fragrance oils. Individual active materials that can be encapsulated include those listed in WO 2016049456, pages 38-50. These active material include flavor or fragrance ingredients, taste masking agents, taste sensates, malodor counteracting agents, vitamins or derivatives thereof, antibacterials, sunscreen actives, antioxidants, anti-inflammatory agents, fungicide, anesthetics, analgesics, antifungal agents, antibiotics, anti-viral agents, anti-parasitic agents, anti-infectious, anti-acne agents, dermatological active ingredients, enzymes and co-enzymes, skin whitening agents, anti-histamines, chemotherapeutic agents, insect repellents, emollient, skin moisturizing agent, wrinkle control agent, UV protection agent, fabric softener active, hard surface cleaning active, skin or hair conditioning agent, animal repellent, vermin repellent, flame retardant, antistatic agent, nanometer to micron size inorganic solid, polymeric or elastomeric particle, and combination thereof.

High performing, high impact fragrances are envisaged. One class of high performing fragrances is described in WO 2018/071897. These fragrances have a high intensity accord containing (i) at least 7 wt % (e.g., 7 to 95 wt %) of Class 1 fragrance ingredients, (ii) 5 to 95 wt % (e.g., 5 to 80 wt %, 10 to 80 wt %, and 10 to 70 wt %) of Class 2 fragrance ingredients, and (iii) 0 to 80 wt % of Class 3 fragrance ingredients, in which the Class 1 fragrance ingredients each have an experimental velocity of 8.5 cm/second or greater, the Class 2 fragrance ingredients each have an experimental velocity of less than 8.5 cm/second and greater than 5 cm/second, and the Class 3 fragrance ingredients each have an experimental velocity of 5 cm/second or less. In some embodiments, the sum of the Class 1 fragrance ingredients, the Class 2 fragrance ingredients, and the Class 3 fragrance ingredients is 100%. In other embodiments, the sum of Class 1 and Class 2 ingredients is 20% to 100 wt %. Other high impact fragrances suitable for use in this invention are those described in WO 1999/065458, U.S. Pat. No. 9,222,055, US 2005/0003975, and WO1997/034987.

In addition to the active materials listed above, the products of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau™ 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

When the active material is a fragrance, it is preferred that fragrance ingredients within a fragrance having a C log P of 0.5 to 15 are employed. For instance, the ingredients having a C log P value between 0.5 to 8 (e.g., between 1 to 12, between 1.5 to 8, between 2 and 7, between 1 and 6, between 2 and 6, between 2 and 5, between 3 and 7) are 25% or greater (e.g., 50% or greater and 90% or greater) by the weight of the fragrance.

It is preferred that a fragrance having a weight-averaged C log P of 2.5 and greater (e.g., 3 or greater, 2.5 to 7, and 2.5 to 5) is employed. The weight-averaged C log P is calculated as follows:

$$C \log P = \{Sum[(W_i)(C \log P)i]\}/\{Sum\ W_i\},$$

in which $W_1$ is the weight fraction of each fragrance ingredient and (C log P)i is the C log P of that fragrance ingredient.

As an illustration, it is preferred that greater than 60 wt % (preferably greater than 80 wt % and more preferably greater than 90 wt %) of the fragrance chemicals have C log P values of greater than 2 (preferably greater than 3.3, more preferably greater than 4, and even more preferably greater than 4.5).

Those with skill in the art will appreciate that many fragrances can be created employing various solvents and fragrance chemicals. The use of a relatively low to intermediate C log P fragrance ingredients will result in fragrances that are suitable for encapsulation. These fragrances are generally water-insoluble, to be delivered through the capsule systems of this invention onto consumer products in different stages such as damp and dry fabric. Without encapsulation, the free fragrances would normally have evaporated or dissolved in water during use, e.g., wash. Though high C log P materials are generally well delivered from a regular (non-encapsulated) fragrance in a consumer product, they have excellent encapsulation properties and are also suitable for encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

In some embodiments, the amount of encapsulated active material is from 5% to 95% (e.g., 10% to 90%, 15% to 85%, and 20% to 80%) by weight of the microcapsule composition. The amount of the capsule wall is from 0.5% to 30% (e.g., 1% to 25%, 2 to 20% and 5 to 15%) also by weight of the microcapsule composition. In other embodiments, the amount of the encapsulated active material is from 15% to 99.5% (e.g., 20% to 98% and 30% to 90%) by weight of the microcapsule, and the amount of the capsule wall is from 0.5% to 85% (e.g., 2 to 50% and 5 to 40%) by weight of the microcapsule.

Adjunct Materials

In addition to the active materials, the present invention also contemplates the incorporation of adjunct materials including solvent, emollients, and core modifier materials in the core encapsulated by the capsule wall. Other adjunct materials are solubility modifiers, density modifiers, stabilizers, viscosity modifiers, pH modifiers, or any combination thereof. These modifiers can be present in the wall or core of the capsules, or outside the capsules in delivery system. Preferably, they are in the core as a core modifier.

The one or more adjunct material may be added in the amount of 0.01% to 40% (e.g., 0.5% to 30%) by weight of the microcapsule.

Suitable examples include those described in WO 2016/049456, pages 55-57 and US 2016/0158121, pages 15-18.

Deposition Aids

An exemplary deposition aid useful in the microcapsule composition of this invention is a copolymer of acrylamide and acrylamidopropyltrimonium chloride. This copolymer facilitates the deposition of the microcapsule onto a hard surface (e.g., hair, skin, fiber, furniture, and floor). The copolymer generally has an average molecular weight (e.g., weight average molecular mass (Mw) determined by size exclusion chromatography) of 2,000 Da to 10,000,000 Da with a lower limit of 2,000 Da, 5,000 Da, 10,000 Da, 20,000 Da, 50,000 Da, 100,000 Da, 250,000 Da, 500,000 Da, or 800,000 Da and an upper limit of 10,000,000 Da, 5,000,000 Da, 2,000,000 Da, 1,000,000 Da, or 500,000 Da (e.g., 500,000 Da to 2,000,000 Da and 800,000 Da to 1,500,000 Da). The charge density of the copolymer ranges from 1 meq/g to 2.5 meq/g, preferably from 1.5 meq/g to 2.2 meq/g. The copolymer of acrylamide and acrylamide-propyltrimonium chloride is commercially available from various vendors such as Ashland as N-Hance® SP-100 and Ciba SALCARE® SC60.

Other suitable deposition aids include anionically, cationically, nonionically, or amphoteric water-soluble polymers. Suitable deposition aids trimonium, methacrylamidopropyl trimethyl ammonium, acrylamidopropyl trimethylammonium, acrylamide, acrylic acid, dimethyl ammonium, xlylose, galactose, hydroxypropylated glucose, hydroxyethylated glucose, hydroxymethylated glucose, vinylamine, ethylenimine, functionalized branched polyethylenimine, vinylformamide, vinylpyrollidone, caprolactone, catechol, vinylalcohol, chitosan, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-79 and hydrolyzed keratin co-polymer, polyquaternium-80, polyquaternium-81, polyquaternium-82, polyquaternium-86, polyquaternium-88, polyquaternium-101, polyvinylamine, polyethyleneimine, a copolymer of vinylamine and vinylformamide, a copolymer of methacrylamidopropyltrimonium chloride and acrylamide, a copolymer of acrylamide and acrylamidopropyltrimonium chloride, a 3-acrylamidopropyl trimethylammonium polymer or its copolymer, a diallyldimethylammoniumchloride polymer and its copolymer, a polysaccharide with saccharide unit functionalized with hydroxypropyl trimmonium, ethyltrimonium chloride methacrylate/hydrolyzed wheat protein copolymer, alkylmonium hydroxypropyl hydrolyzed protein, and combinations thereof. More examples of the deposition aids are described in WO 2016049456, pages 13-27; US 2013/0330292; US 2013/0337023; and US 2014/0017278.

Additional depositional aids are those cationic polymers described in WO2016032993. These cationic polymers are typically characterized by a relatively high charge density (e.g., from 4 meq/g, or from 5 meq/g, or from 5.2 meq/g to 12 meq/g, or to 10 meq/g, or to 8 meq/g or to 7 meq/g, or to 6.5 meq/g. The cationic polymers are comprised of structural units that are nonionic, cationic, anionic, or mixtures thereof. In some aspects, the cationic polymer comprises from 5 mol % to 60 mol %, or from 15 mol % to 30 mol %, of a nonionic structural unit derived from a monomer selected from the group consisting of (meth)acrylamide, vinyl formamide, N,N-dialkyl acrylamide, N,N-dialkylmethacrylamide, $C_1$-$C_{12}$ alkyl acrylate, $C_1$-$C_{12}$ hydroxyalkyl acrylate, polyalkylene glyol acrylate, $C_1$-$C_{12}$ alkyl methacrylate, $C_1$-$C_{12}$ hydroxyalkyl methacrylate, polyalkylene glycol methacrylate, vinyl acetate, vinyl alcohol, vinyl formamide, vinyl acetamide, vinyl alkyl ether, vinyl pyridine, vinyl pyrrolidone, vinyl imidazole, vinyl caprolactam, and mixtures thereof.

In some aspects, the cationic polymer comprises a cationic structural unit at the level of 30 mol % to 100 mol %, or 50 mol % to 100 mol %, or 55 mol % to 95 mol %, or 70 mol % to 85 mol % by mass of the cationic polymer. The cationic structural unit is typically derived from a cationic monomer such as N,N-dialkylaminoalkyl methacrylate, N,N-dialkylaminoalkyl acrylate, N,N-dialkylaminoalkyl acrylamide, N,N-dialkylaminoalkylmethacrylamide, methacylamidoalkyl trialkylammonium salts, acrylamidoalkylltrialkylamminium salts, vinylamine, vinylimine, vinyl imidazole, quaternized vinyl imidazole, diallyl dialkyl ammonium salts, and mixtures thereof Preferably, the cationic monomer is selected from the group consisting of diallyl dimethyl ammonium salts (DADMAS), N,N-dimethyl aminoethyl acrylate, N,N-dimethyl aminoethyl methacrylate (DMAM), [2-(methacryloylamino)ethyl]tri-methylammonium salts, N,N-dimethylaminopropyl acrylamide (DMAPA), N,N-dimethylaminopropyl methacrylamide (DMAPMA), acrylamidopropyl trimethyl ammonium salts (APTAS), methacrylamidopropyl trimethylammonium salts (MAPTAS), quaternized vinylimidazole (QVi), and mixtures thereof.

In some aspects, the cationic polymer comprises an anionic structural unit at a level of 0.01 mol % to 15 mol %, 0.05 mol % to 10 mol %, 0.1 mol % to 5 mol %, or 1% to 4% of by mass of the cationic polymer. In some aspects, the anionic structural unit is derived from an anionic monomer selected from the group consisting of acrylic acid (AA), methacrylic acid, maleic acid, vinyl sulfonic acid, styrene sulfonic acid, acrylamidopropylmethane sulfonic acid (AMPS) and their salts, and mixtures thereof.

Exemplary cationic polymers are polyacrylamide-co-DADMAS, polyacrylamide-co-DADMAS-co-acrylic acid, polyacrylamide-co-APTAS, polyacrylamide-co-MAPTAS, polyacrylamide-co-QVi, polyvinyl formamide-co-DADMAS, poly(DADMAS), polyacrylamide-co-MAPTAS-coacrylic acid, polyacrylamide-co-APTAS-co-acrylic acid, and mixtures thereof.

The deposition aid is generally present at a level of 0.01% to 50% (with a lower limit of 0.01%, 0.05%, 0.1%, 0.5%, 1%, 2%, or 5% and an upper limit of 50%, 40%, 30%, 20%, 15%, or 10%, e.g., 0.1% to 30%, 1% to 20%, 2% to 15%, and 5% to 10%) by weight of the microcapsule composition. In a consumer product such as a shampoo, the deposition aid is generally present at a level of 0.001% to 20% (with a lower limit of 0.001%, 0.005%, 0.01%, 0.02%, or 0.05% and an upper limit of 20%, 15%, 10%, 5%, 2%, or 1%, e.g., 0.005% to 10%, 0.01% to 5%, and 0.02% to 0.5%) by weight of the shampoo composition. The capsule deposition aid can be added during the preparation of the microcapsules or it can be added after the microcapsules have been made.

A second capsule deposition aid from 0.01% to 25%, more preferably from 5% to 20% can be added to the microcapsule composition. The second capsule formation deposition aid can be selected from the above-described deposition aid.

Additional Components

The microcapsule composition of this invention can include one or more non-confined or unencapsulated active materials from 0.01 to 50%, more preferably from 5 to 40%.

The capsule delivery system can also contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. More exemplary delivery systems that can be incorporated are coacervate capsules, cyclodextrin delivery systems, and pro-perfumes.

Examples of additional components include those described in US 2016/0158121.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethyl-ammonium ion). A precursor can be ester and another suitable derivative, which, during the process of preparing a capsule composition of this invention, is capable of converting to the compound, polymer, or agent and being used in preparing the capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine includes L-ornithine and its salts/hydrates (e.g., monohydrochloride) and D-ornithine and its salts/hydrates (e.g., monohydrochloride).

The microcapsule composition of this invention can be a slurry containing in a solvent (e.g., water) the capsule at a level 0.1% to 80% (preferably 1% to 65% and more preferably 5% to 45%) by weight of the capsule delivery system. An exemplary microcapsule composition of this invention contains a plurality of microcapsules each dispersed in an aqueous phase and is stable for at least 7 days (e.g., at least 10 days, at least 30 days, and at least 60 days) at 40° C. Stability is measured (e.g., in a graduated cylinder) by the separation of a clear aqueous phase from the microcapsule composition. The microcapsule composition is deemed stable if, by volume of the microcapsule composition, less than 10% of a clear aqueous phase is separated. The microcapsule composition is considered stable when (i) the composition has a viscosity of 3000 cP or less (e.g., 2000 cP or less) and (ii) 20% or less (e.g., 15% or less, and 10% or less) water by volume of the composition is separated from the composition. The volume of the separated water can be readily measured by a convention method, e.g., a graduated cylinder.

Microcapsule compositions are known to have the tendency to form into gels, unsuitable for use in many consumer products. The viscosity of the gelled-out composition increases to at least 3000 centipoise (cP) (e.g., at least 6000 cP). The viscosity can be readily measured on rheometer, for example a RheoStress™ 1 instrument (Commercially available from ThermoScientific), using rotating disks at a shear rate of 21 $s^{-1}$ and a temperature of 25° C.

In some embodiments, the microcapsule composition is purified by washing the capsule slurry with water until a neutral pH (pH of 6 to 8) is achieved. For the purposes of the present invention, the capsule suspension can be washed using any conventional method including the use of a separatory funnel, filter paper, centrifugation and the like. The capsule suspension can be washed one, two, three, four, five, six, or more times until a neutral pH, e.g., pH 6-8 and 6.5-7.5, is achieved. The pH of the purified capsules can be determined using any conventional method including, but not limited to pH paper, pH indicators, or a pH meter.

A capsule composition is "purified" in that it is 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments of this invention, the purification of the capsules includes the additional step of adding a salt to the capsule suspension prior to the step of washing the capsule suspension with water. Exemplary salts of use in this step of the invention include, but are not limited to, sodium chloride, potassium chloride or bi-sulphite salts. See US 2014/0017287.

The microcapsule composition of this invention can also be dried, e.g., spray dried, heat dried, and belt dried, to a solid form. In a spray drying process, a spray dry carrier is added to a microcapsule composition to assist the removal of water from the slurry. See US20120151790, US20140377446, US20150267964, US20150284189, and US20160097591.

According to one embodiment, the spray dry carriers can be selected from the group consisting of carbohydrates such as chemically modified starches and/or hydrolyzed starches, gums such as gum Arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1% to 50%, more preferably from 5% to 20%, by weight of the microcapsule composition in slurry.

Optionally, a free flow agent (anticaking agent) of silicas which may be hydrophobic (i.e. silanol surface treated with halogen silanes, alkoxysilanes, silazanes, siloxanes, etc. such as Sipernat® D17, Aerosil® R972 and R974 (available from Degussa), etc.) and/or hydrophilic such as Aerosil® 200, Sipernat® 22S, Sipernat® 50S, (available from Degussa), Syloid® 244 (available from Grace Davison), may be present from 0.01% to 10%, more preferable from 0.5% to 5%, by weight of the microcapsule composition in slurry.

Humectants and viscosity control/suspending agents can also be added to facilitate spray drying. These agents are disclosed in U.S. Pat. Nos. 4,446,032 and 6,930,078. Details of hydrophobic silica as a functional delivery vehicle of active materials other than a free flow/anticaking agent are disclosed in U.S. Pat. Nos. 5,500,223 and 6,608,017.

The spray drying inlet temperature is in the range of 150° C. to 240° C., preferably between 170 and 230° C., more preferably between 190° C. and 220° C.

As described herein, the spray-dried microcapsule composition is well suited for use in a variety of all dry (anhydrous) products: powder laundry detergent, fabric softener dryer sheets, household cleaning dry wipes, powder dish detergent, floor cleaning cloths, or any dry form of personal care products (e.g. shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The microcapsule composition can also be sprayed as a slurry onto a consumer product, e.g., a fabric care product. By way of illustration, a microcapsule slurry is sprayed onto a detergent powder during blending to make granules. See US 2011/0190191. In order to increase fragrance load, water-absorbing material, such as zeolite, can be added to the delivery system.

Alternatively, granulates in a consumer product are prepared in a mechanical granulator in the presence of a granulation auxiliary such as non-acid water-soluble organic crystalline solids. See WO 2005/097962.

Zeta Potentials and Rupture Forces

The microcapsule of this invention can be positively or negatively charged with a zeta potential in the range of −200 mV to +200 mV, e.g., at least 10 mV, at least 25 mV, at least 40 mV, 25 mV to 200 mV, and 40 mV to 100 mV.

Zeta potential is a measurement of electrokinetic potential in the microcapsule. From a theoretical viewpoint, zeta potential is the potential difference between the water phase (i.e., the dispersion medium) and the stationary layer of water attached to the surface of the microcapsule.

The zeta potential is an important indicator of the stability of the microcapsule in compositions or consumer products. Typically, a microcapsule having a zeta potential of 10 mV to 25 mV shows a moderate stability. Similarly, a microcapsule having a zeta potential of 25 mV to 40 mV shows a good stability and a microcapsule having a zeta potential of 40 mV to 100 mV shows excellent stability. Not to be bound by any theory, the microcapsule of this invention has a desirable zeta potential making it suitable for use in consumer products with improved stability.

The zeta potential can be calculated using theoretical models and an experimentally-determined electrophoretic mobility or dynamic electrophoretic mobility. The zeta potential is conventionally measured by methods such as microelectrophoresis, or electrophoretic light scattering, or electroacoustic phenomena. For more detailed discussion on measurement of zeta potential, see Dukhin and Goetz, "Ultrasound for characterizing colloids", Elsevier, 2002.

The microcapsule of this invention has a fracture strength of 0.2 MPa to 80 MPa (e.g., 0.5 MPa to 60 MPa, 1 MPa to 50 MPa, and 5 MPa to 30 MPa). The fracture strength of each microcapsule is calculated by dividing the rupture force (in Newtons) by the cross-sectional area of the respective microcapsule ($\pi r^2$, where r is the radius of the particle before compression). The measurement of the rupture force and the cross-sectional area is performed following the methods described in Zhang et al., *J. Microencapsulation* 18(5), 593-602 (2001).

The microcapsule of this invention has a rupture force of less than 10 millinewtons ("mN") such as 0.1 mN to 10 mN, 0.2 mN to 8 mN, 0.3 mN to 5 mN, 0.1 mN to 2 mN, 0.1 mN, 0.5 mN, 1 mN, 2 mN, 5 mN, and 8 mN. The rupture force is the force needed to rupture the microcapsules. Its measurement is based on a technique known in the art as micro-manipulation. See Zhang et al., *Journal of Microencapsulation* 16(1), 117-124 (1999).

The microcapsule composition of this invention can be a slurry or suspension, wherein the microcapsule is in a solvent (e.g., water) at a level 0.1% to 80% (preferably 1% to 65% and more preferably 5% to 45%) by weight of the microcapsule composition.

Microcapsule compositions are known to have the tendency to form into gels, unsuitable for use in many consumer products. The viscosity of the gelled-out composition increases to at least 3000 centipoise (cP) (e.g., at least 6000 cP). The viscosity can be readily measured on rheometer, for example a RheoStress™ 1 instrument (Commercially available from ThermoScientific), using rotating disks at a shear rate of 21 s$^{-1}$ and a temperature of 25° C. In certain embodiments, the viscosity of a microcapsule composition of this invention is less than 3000 cP at a shear rate of 21 s$^{-1}$ and a temperature of 25° C.

Stability of a microcapsule can be assessed using a number of different approaches including physical stability and/or storage stability. When assessing physical stability, an exemplary microcapsule composition may be dispersed in an aqueous phase and shown to be stable for at least 7 days (e.g., at least 10 days, at least 30 days, and at least 60 days) at 40° C. Stability is measured (e.g., in a graduated cylinder) by the separation of a clear aqueous phase from the microcapsule composition. The microcapsule composition is deemed stable if, by volume of the microcapsule composition, less than 10% of a clear aqueous phase is separated. The microcapsule composition is considered stable when (i) the composition has a viscosity of 3000 cP or less (e.g., 2000 cP or less) and (ii) 20% or less (e.g., 15% or less, and 10% or less) water by volume of the composition is separated from the composition. The volume of the separated water can be readily measured by a convention method, e.g., a graduated cylinder.

When assessing storage stability, fragrance retention within the microcapsule may be measured directly after storage at a desired temperature and time periods such as four weeks, six weeks, two months, three months or more in a consumer product base. The preferred manner is to measure total headspace of the consumer product at the specified time and to compare the results to the headspace of a control consumer product made to represent 0% retention via direct addition of the total amount of fragrance present. Alternatively, the consumer product may be performance tested after the storage period and the performance compared to the fresh product, either analytically or by sensory evaluation. This measurement often involves either measuring the fragrance headspace over a substrate used with the product, or odor evaluation of the same substrate. In certain embodiments, retention of the active material in the core of the instant microcapsules is assessed in a consumer product base, e.g., under storage conditions such as at a temperature in the range of 25° C. to 40° C., or more preferably in the range of 30° C. to 37° C., or most preferably 37° C., for an extended period of time of at least 2 weeks, 4 weeks, 6 weeks, 8 weeks, 16 weeks, or 32 weeks. In certain embodiments, the microcapsules of this invention retain at least 40%, 45%, 50%, 55%, 60%, 65%, 70%, 75%, 80%, 85%, 90%, 95%, or 99% of the active material when added to a consumer product base. In particular embodiments, the microcapsules of this invention, when added to a consumer product base, retain between 40% and 90% of the active material after being stored at 37° C. for at least 4 weeks, 8 weeks or 12 weeks. Alternatively stated, the microcapsules of this invention lose less than 50% of the active material due to leakage when added to a consumer product base and stored for 8 weeks at 37° C.

Using a process of this invention, a relative high encapsulation efficiency is achieved. "Encapsulation efficiency" or "microencapsulation efficiency" or "MEE" represents the proportion of the active material core that is not available to an extracting solvent under specified test conditions. In accordance with the method of this invention, microencapsulation efficiencies in the range of 50% to 99.9% are attainable, or more preferably 60% to 99.7%. In particular, encapsulation efficiencies of at least 90%, 92%, 94%, 96%, 98%, or 99% are achieved.

In some embodiments, the microcapsule composition is purified by washing the capsule slurry with water until a neutral pH (pH of 6 to 8) is achieved. For the purposes of the present invention, the capsule suspension can be washed using any conventional method including the use of a separatory funnel, filter paper, centrifugation and the like. The capsule suspension can be washed one, two, three, four, five, six, or more times until a neutral pH, e.g., pH 6-8 and 6.5-7.5, is achieved. The pH of the purified capsules can be determined using any conventional method including, but not limited to pH paper, pH indicators, or a pH meter.

A capsule composition is "purified" in that it is at least 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., excess cross-linking agent and the like. See US 2014/0017287.

The microcapsule composition of this invention can also be dried, e.g., spray-dried, heat dried, and belt dried, to a solid form. In a spray drying process, a spray-dry carrier is added to a microcapsule composition to assist the removal of water from the slurry. See US20120151790, US20140377446, US20150267964, US20150284189, and US20160097591.

According to one embodiment, the spray dry carriers can be selected from the group of carbohydrates such as chemically modified starches and/or hydrolyzed starches, gums such as gum Arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1 to 50%, more preferably from 5 to 20%, by weight of the microcapsule composition in slurry.

In certain embodiments, a microcapsule composition that is dried in the presence of a carrier, which further includes an unencapsulated or non-confined active material. Such compositions can be prepared by combining an aqueous carrier solution, in particular a starch solution; preparing an oil phase containing an active material (e.g., a flavor or fragrance); emulsifying the oil phase with the aqueous carrier solution to obtain an emulsion; mixing the emulsion with a biodegradable core-shell microcapsule composition; and spray drying the resulting mixture.

Optionally, a free flow agent (anticaking agent) may be included in the microcapsule composition. Free flow agents of particular use include silicas, which may be hydrophobic silicas (i.e., silanol surface treated with halogen silanes, alkoxysilanes, silazanes, and siloxanes sold under the trademarks SIPERNAT® D17, AEROSIL® R972 and R974 by Degussa) and/or hydrophilic silicas (i.e., silicas sold under the trademarks AEROSIL® 200, SIPERNAT® 22S, SIPERNAT® 50S, by Degussa, or SYLOID® 244 by Grace Davison). Free flow agents may be present from 0.01 to 10%, more preferable from 0.5 to 5%, by weight of the microcapsule composition in slurry.

Humectants and viscosity control/suspending agents can also be added to facilitate spray drying. These agents are disclosed in U.S. Pat. Nos. 4,446,032 and 6,930,078. Details of hydrophobic silica as a functional delivery vehicle of active materials other than a free flow/anticaking agent are disclosed in U.S. Pat. Nos. 5,500,223 and 6,608,017.

The spray drying inlet temperature for spray drying the microcapsule composition may be in the range of 150° C. to 240° C., preferably between 170° C. and 230° C., more preferably between 190° C. and 220° C.

Alternatively, granulates for use in a consumer product may be prepared in a mechanical granulator in the presence of a granulation auxiliary such as non-acid water-soluble organic crystalline solids. See WO 2005/097962.

Applications

The microcapsule of the present invention is well-suited for use, without limitation, in the following consumer products at a level of 0.01 wt % to 98 wt % (e.g., 0.1 wt %, 0.5 wt %, 1 wt %, 2 wt %, 5 wt %, 10 wt %, 15 wt %, 30 wt %, 40 wt %, 50 wt %, 60 wt %, 70 wt %, 80 wt %, 90 wt % and 95 wt %): a baby care product, a diaper rash cream or balm, a baby powder, a diaper, a bib, a baby wipe, a cosmetic preparation, a powder foundation, a liquid foundation, an eye shadow, a lipstick or lip balm, a home care product, an all-purpose cleaner, a bathroom cleaner, a floor cleaner, a window cleaner, a plastics polish, a bleach, a toilet cleaner, a toilet rimblock, a bath tissue, a paper towel, a disposable wipe, liquid air freshener, air freshener spray, a spray dispenser product, an incense stick, a rug deodorizer, a candle, a room deodorizer, a liquid dish detergent, an automatic dish detergent, a powder dish detergent, a leather detergent, a tablet dish detergent, a paste dish detergent, a unit dose tablet or capsule, a flavor, a beverage flavor, a diary flavor, a fruit flavor, a miscellaneous flavor, a sweet goods flavor, a tobacco flavor, a toothpaste flavor, a chewing gum, a breath freshener, an orally dissolvable strips, a chewable candy, a hard candy, an oral care product, a tooth paste, a toothbrush, a dental floss, an oral rinse, an tooth whitener, a denture adhesive, a health care device, a tampon, a feminine napkin, an anti-inflammatory balm, an anti-inflammatory ointment, an anti-inflammatory spray, a disinfectant, a personal care product, a soap, a bar soap, a liquid soap, a bath fragrance, a body wash, a non-aerosol body spray, a body milk, a cleanser, a body cream, a hand sanitizer, a hand wash, a functional product base, a sunscreen lotion, a sunscreen spray, a deodorant, an anti-perspirant, an roll-on product, an aerosol product, a natural spray product, a wax-based deodorant, a glycol type deodorant, a soap type deodorant, a facial lotion, a body lotion, a hand lotion, a miscellaneous lotion, a body powder, a shave cream, a shave gel, a shave butter, a bath soak, a shower gel, an exfoliating scrub, a foot cream, a facial tissue, a cleansing wipe, a talc product, a hair care product, a hair care with ammonia, a shampoo, a hair conditioner, a hair rinse, a hair refresher, a hair fixative or styling aid, a hair bleach, a hair dye or colorant, a fabric care product, a fabric softener, a liquid fabric softener, a fabric softener sheet, a drier sheet, a fabric refresher, an ironing water, a detergent, a laundry detergent, a liquid laundry detergent, a powder laundry detergent, a tablet laundry detergent, a laundry detergent bar, a laundry detergent cream, a hand wash laundry detergent, a scent booster, scent drops (a liquid fragrance composition), a fragrance, a cologne, compounds, an encapsulated fragrance, a fine fragrance, a men's fine fragrance, a women's fine fragrance, a perfume, a solid perfume, an Eau De Toilette product, a natural spray product, a perfume spray product, an insect repellent product, or a wildlife scent.

Advantageously, the microcapsules of the invention do not tend to form visible aggregates (e.g., greater than 100 μm) and can readily be added to the base of a fabric softener, detergent, AP/deodorant, fine, personal care leave on, personal care rinse off, or home care product. As used herein, a "consumer product base" refers to a composition for use as a consumer product to fulfill specific actions, such as cleaning, softening, and caring or the like. Such consumer product bases can include surfactants, alkali materials, acidic materials, dyes, unencapsulated (neat) fragrances, and the like. As such, it is contemplated that certain biopolymer wall materials will be more compatible with certain consumer product bases.

As described herein, a spray-dried microcapsule composition is well suited for use in a variety of all dry (anhydrous) products: powder laundry detergent, fabric softener dryer sheets, household cleaning dry wipes, powder dish detergent, floor cleaning cloths, or any dry form of personal care products (e.g., shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The microcapsule composition of this invention can be added to a consumer product base directly or be printed onto a product base or a movable product conveyor (e.g., a non-stick belt) for drying. See International Application Publication WO2019212896A1. In a typical printing system, the microcapsule composition is printed onto a movable product conveyor that directly receives the printed microcapsule, which is then dried on the movable product conveyor to produce a dried product. Additional carriers and solvent can be added to the microcapsule composition before printing. In some embodiments, the viscosity of the microcapsule composition is adjusted to more than 500 cP or more than 1000 cP with a viscosity modifier. With reference to the print assembly, the print assembly can include a print head or array of nozzles and optionally be adapted to print the microcapsule in a dot pattern (e.g., arranged to facilitate drying, post-processing, and product quality). Optional features of the system include, a dehumidifier configured to supply desiccated air to the drying component; a supplemental energy source (e.g. a radiant heat source), for facilitating drying of the printed microcapsule; and/or a product discharge component for removing dried product from the movable product conveyor.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For Example, a value disclosed as "50%" is intended to mean "about 50%."

The terms "include," "includes," and "including," are meant to be non-limiting.

The terms "capsule" and "microcapsule" herein are used interchangeably.

The term "curing" as used polymer chemistry and process engineering refers to a toughening or hardening process of a polymer by cross-linking of polymer chains, brought about by heat, chemical additives, or light radiation.

As used herein, a "core-shell microcapsule," or more generically a "microcapsule" or "capsule," is a substantially spherical structure having a well-defined core and a well-defined envelope or wall. Ideally, the wall protects the core against deterioration by oxygen, moisture, light, and effect of other compounds or other factors; limits the losses of volatile core materials; and releases the core material under desired conditions. In this respect, the core-shell microcapsules of this invention provide controlled release of the active material. As used herein, "controlled release" refers to retention of the active material in the core until a specified triggering condition occurs. Such triggers include, e.g., friction, swelling, a pH change, an enzyme, a change in temperature, a change in ionic strength, or a combination thereof.

The invention is described in greater detail by the following non-limiting examples. Without further elaboration, it is believed that one skilled in the art can, based on the description herein, utilize the present invention to its fullest extent. All publications cited herein are incorporated by reference in their entirety.

Example 1: Microcapsule 1 Prepared from Moderately-Denatured Pea Protein

An oil phase was first prepared by mixing 216 grams (g) of a model fragrance and 45 g of caprylic/capric triglyceride (a core solvent, commercially available under the trade name of NEOBEE® oil M-5, Stepan, Chicago, IL), and an aromatic polyisocyanate (3.5 g) (trimethylol propane-adduct of xylylene diisocyanate, commercially available as 50% solution in benzyl benzoate under the trade name of Takenate™ D-110N, Mitsui Chemicals Inc., Japan). In a separate beaker, an aqueous solution was obtained by mixing 11 g of a pea protein isolate (Roquette, Lestrem, France) in 316 g of water. The oil phase was then emulsified into the aqueous phase to form an oil-in-water emulsion using an ultra turrax mixer at a shear rate of 5000 Revolutions Per Minute (RPM). The oil-in-water emulsion was then cured at 55° C. for 2 hours.

Microcapsule 1 thus prepared had 5.25% of the microcapsule wall and 94.75% of the microcapsule core including 77.4% of the fragrance in the core, all by weight of the microcapsule.

The formulation of Microcapsule 1 is summarized in Table 1. The percentage of each component was calculated based on the microcapsule wall and core materials, excluding water. In addition, the wall of Microcapsule 1 contained 76% of the first moiety derived from the pea protein and 24% of the second moiety derived from the polyisocyanate, by weight of the microcapsule wall. The crosslinking of protein to wall was confirmed by a size-exclusion chromatography (SEC).

TABLE 1

| Microcapsule 1 dispersed in 316 g of water Shearing rate 5000 RPM, curing 55° C., 2 hours Microcapsule size: 25 μm in diameter | | |
|---|---|---|
| Component | Amount | % by weight of microcapsule |
| Microcapsule Core: | | (94.75%) |
| Fragrance | 216 g | 77.4% |
| Neobee M5 oil | 45 g | 16.1% |
| Benzyl benzoate[a] | 3.5 g | 1.25% |
| Microcapsule Wall | | (5.25%) |
| pea protein isolate | 11 g | 4% |
| Polyisocyanate[b] | 3.5 g | 1.25% |
| Total | 279 g | (100%) |

[a]Solvent for polyisocyanate.
[b]Takenate™ D-110N by Mitsui Chemicals Inc., Japan.

Microcapsules 1a-1c were prepared following the same process except that different shearing rates were used: 8000 RPM, 10000 RPM, and 13500 RPM. Microcapsules can be successfully prepared using a shearing rate of 3000 RPM to 15000 RPM, preferably at 3500 RPM to 7500 RPM, and more preferably 4000 RPM to 6500 RPM.

Examples 2-8

Microcapsules 2-8 were prepared following the procedure described in Example 1 with various proteins. See Tables 2-8 for the formulation of each microcapsule. The percentages of the protein and the polyisocyanate moieties were given in Table 9 below.

As a summary, the microcapsules contained by weight of the microcapsule:

a) 89% to 98% of the microcapsule core,
  i. 73% to 80% of a fragrance
b) 2% to 11% microcapsule Wall
  i. 2% to 7.5% of a protein
  ii. 0.65% to 1.9% of a polyisocyanatea.

TABLE 2

| Microcapsule 2 dispersed in 316 g of water Shearing rate 10000 RPM, curing 55° C., 2 hours | | |
|---|---|---|
| Component | Amount | % by weight of microcapsule |
| Microcapsule Core: | | (90.6%) |
| Fragrance | 216 g | 73.4% |
| Neobee M5 oil | 45 g | 15.3% |
| Benzyl benzoate | 5.5 g | 1.9% |

TABLE 2-continued

Microcapsule 2 dispersed in 316 g of water
Shearing rate 10000 RPM, curing 55° C., 2 hours

| Component | Amount | % by weight of microcapsule |
|---|---|---|
| Microcapsule Wall | | (9.4%) |
| pea protein isolate | 22 g | 7.5% |
| Polyisocyanate[a] | 5.5 g | 1.9% |
| Total | 294 g | (100%) |

[a]Takenate™ D-110N.

TABLE 3

Microcapsule 3 Dispersed in 316 g of water
Shearing rate 5000 RPM, curing 55° C., 2 hours

| Component | Amount | % by weight of microcapsule |
|---|---|---|
| Microcapsule Core: | | (97.35%) |
| Fragrance | 216 g | 80% |
| Neobee M5 oil | 45 g | 16.7% |
| Benzyl benzoate[b] | 1.75 g | 0.65% |
| Microcapsule Wall | | (2.65%) |
| pea protein isolate | 5.5 g | 2% |
| Polyisocyanate | 1.75 g | 0.65% |
| Total | 270 g | (100%) |

[a]Takenate™ D-110N.

TABLE 4

Microcapsule 4 dispersed in 323.8 g of water
DABCO (0.7 g) was added to catalyze the crosslinking reaction.
Shearing rate 5000 RPM, curing 90° C., 3 hours

| Component | Amount | % by weight of microcapsule |
|---|---|---|
| Microcapsule Core: | | 97.35% |
| Fragrance | 216 g | 80% |
| Neobee M5 oil | 45 g | 16.7% |
| Microcapsule Wall | | 2.65% |
| pea protein isolate | 11 g | 2% |
| Polyisocyanate[a] | 3.5 g | 0.65% |
| Total | 275.5 g | 100% |

[a]A hydrophilic aliphatic polyisocyante based on hexamethylene diisocyanate (HDI) available under the trade name of Bayhydur® 305 from Covestro AG, Leverkusen, Germany. The polyisocyanate was dissolved in the aqueous phase.

TABLE 5

Microcapsule 5 dispersed in 316 g of water
Shearing rate 5000 RPM, curing 55° C., 2 hours

| Component | Amount | % by weight of microcapsule |
|---|---|---|
| Microcapsule Core: | | (94.75%) |
| Fragrance | 216 g | 77.4% |
| Neobee M5 oil | 45 g | 16.1% |
| Benzyl benzoate | 3.5 g | 1.25% |
| Microcapsule Wall | | (5.25%) |
| Soy protein isolate[a] | 11 g | 4% |
| Polyisocyanate[b] | 3.5 g | 1.25% |
| Total | 279 g | (100%) |

[a]Roquette & Barentz, Hoofddorp, Netherlands
[b]Takenate™ D-110N by Mitsui Chemicals Inc., Japan.

TABLE 6

Microcapsule 6 dispersed in 316 g of water
Shearing rate 10000 RPM, curing 55° C., 2 hours

| Component | Amount | % by weight of microcapsule |
|---|---|---|
| Microcapsule Core: | | (90.6%) |
| Fragrance | 216 g | 73.4% |
| Neobee M5 oil | 45 g | 15.3% |
| Benzyl benzoate | 5.5 g | 1.9% |
| Microcapsule Wall | | (9.4%) |
| Soy protein isolate[a] | 22 g | 7.5% |
| Polyisocyanate[b] | 5.5 g | 1.9% |
| Total | 294 g | (100%) |

[a]Roquette & Barentz, Hoofddorp, Netherlands
[b]Takenate™ D-110N by Mitsui Chemicals Inc., Japan.

TABLE 7

Microcapsule 7 dispersed in 296 g of water
Shearing rate 12000 RPM, curing 55° C., 2 hours
Capsule size 7 μm in diameter

| Component | Amount | % by weight of microcapsule |
|---|---|---|
| Microcapsule Core: | | (90.5%) |
| Fragrance | 216 g | 74% |
| Neobee M5 oil | 45 g | 15.3% |
| Benzyl benzoate | 3.5 g | 1.2% |
| Microcapsule Wall | | (9.5%) |
| Soy protein isolate[a] | 22 g | 7.5% |
| Polyisocyanate[b] | 3.5 g | 1.2% |
| Tannic acid[c] | 2.4 g | 0.8% |
| Total | 292.4 g | (100%) |

[a]Roquette & Barentz, Hoofddorp, Netherlands
[b]Takenate™ D-110N by Mitsui Chemicals Inc., Japan.
[c]Tannal® 2 Ajinomoto Natural Specialties, Tokyo, Japan

TABLE 8

Microcapsule 8 dispersed in 282 g of water
Shearing rate 12000 RPM, curing 55° C., 2 hours
Capsule size, 7 μm in diameter

| Component | Amount | % by weight of microcapsule |
|---|---|---|
| Microcapsule Core: | | (89.4%) |
| Fragrance | 216 g | 73% |
| Neobee M5 oil | 45 g | 15.2% |
| Benzyl benzoate | 3.5 g | 1.2% |
| Microcapsule Wall | | (10.6%) |
| Soy protein isolate[a] | 22 g | 7.4% |
| Polyisocyanate[b] | 3.5 g | 1.2% |
| Tannic acid[c] | 6 g | 2% |
| Total | 296 g | (100%) |

[a]Roquette & Barentz, Hoofddorp, Netherlands
[b]Takenate™ D-110N by Mitsui Chemicals Inc., Japan.
[c]Tannal® 2 Ajinomoto Natural Specialties, Tokyo, Japan

TABLE 9

Wall components, wt % by the weight of the microcapsule wall

| Microcapsule | Protein, wt % | Polyisocyanate, wt % | Tannic acid, wt % |
|---|---|---|---|
| 1 | 76 | 24 | — |
| 2 | 80 | 20 | — |
| 3 | 75 | 25 | — |
| 4 | 75 | 25 | — |
| 5 | 76 | 24 | — |
| 6 | 80 | 20 | — |
| 7 | 79 | 12.6 | 8.4 |
| 8 | 69.8 | 11.3 | 18.9 |

Examples 9-10

Two microcapsule compositions of this invention were prepared following the procedure described in Example 1 using a different shearing rate.

Microcapsule composition 9 contained a microcapsule having a particle size of 17 μm (in diameter). The microcapsule in Microcapsule Composition 10 had a particle size of 30 μm. Their % deformation, stress, and nominal tension were evaluated following the methods described in Min Liu, "Understanding the Mechanical Strength of Microcapsules and Their Adhesion on Fabric Surfaces" (PhD diss., University of Birmingham, 2010). Table 10 below summarizes the results.

TABLE 10

| Composition | Particle size μm | Deformation % | Stress MPa | Nominal tension N/m |
|---|---|---|---|---|
| 9 | 17 | 34 | 0.06 | 0.25 |
| 10 | 30 | 55 | 0.3 | 2.3 |

The results showed that it is preferably to have a particle size of 20 μm or greater for the microcapsule to be strong enough for the damp and dry performance in a laundry cycle.

Performance Evaluation from Fabric Conditioner

Microcapsules were incorporated into a fabric conditioner base and a hair conditioner base at a dosage of 1% Neat Oil Equivalence and evaluated for their fragrance performance using a LMC scale. The microcapsule stability in the bases was also tested at various temperature (e.g., 5° C. and 37° C.) for a prolonged period of time (e.g., 8 weeks). The tested microcapsules showed high fragrance performance and good stability.

Examples 11-19

Microcapsule compositions 11-19 of this invention were prepared following the procedure described in Example 1 with the components shown in Table 11 below. Comparative Compositions C1-C8 were also prepared in a similar way. In all these examples, the polyisocyanate is trimethylol propane-adduct of xylylene diisocyanate, commercially available from Mitsui Chemicals America, Inc under the trademark of Takenate™ D-110N.

The free oil, particle size, and fragrance intensity are summarized in this table. In some examples, the fragrance intensity at toss was not evaluated.

TABLE 11

| Example | Components wt %[1] | Free oil % | Particle size μm | Fragrance intensity Pre-rub/toss/post-rub |
|---|---|---|---|---|
| 11 | Pea Protein, 1.8%<br>Polyisocyanate, 1%<br>Fragrance, 36%<br>Core solvent,[2] 7.37% | 0.9 | 26 | 8.1/9.7/12.1 |
| 12 | Pea Protein, 1.8%<br>Polyisocyanate, 0.5%<br>Fragrance, 36%<br>Core solvent, 7.8% | 1.8 | 37 | 7.7/8.6/10.1 |
| C1 | Pea Protein, 0%<br>Polyisocyanate, 1%<br>Fragrance, 31.2%<br>Core solvent,[2] 7.8% | <0.1 | 15 | 0.4/NA/3.8 |
| 13 | Pea Protein, 0.9%<br>Polyisocyanate, 1%<br>Guanidine, 0.65%<br>Emulsifier,[3] 0.6%<br>Fragrance, 36%<br>Core solvent,[2] 7.37% | 0.3 | 49 | 0.4/NA/5.6 |
| C2 | Pea Protein, 0.9%<br>Polyisocyanate, 1%<br>Guanidine, 0.65%<br>Emulsifier,[3] 0.6%<br>Fragrance, 36%<br>Core solvent,[2] 7.37% | >5 | 25 | Not evaluated.<br>Free oil is too high. |
| 14 | Pea Protein, 0.9%<br>Polyisocyanate, 1%<br>Emulsifier,[4] 1%<br>Fragrance, 36%<br>Core solvent,[2] 7.37% | 0.3 | 23 | 1.1/NA/4.8 |

TABLE 11-continued

| Example | Components wt %[1] | Free oil % | Particle size μm | Fragrance intensity Pre-rub/toss/post-rub |
|---|---|---|---|---|
| 15 | Pea Protein, 0.9% Polyisocyanate, 1% Guanidine, 0.65% Emulsifier,[4] 1% Fragrance, 36% Core solvent,[2] 7.37% | 0.3 | 56 | 1/NA/5 |
| C4 | Pea Protein, 0.9% Polyisocyanate, 1% HMDA,[5] 1.3% Emulsifier,[4] 1% Fragrance, 36% Core solvent,[2] 7.37% | >5 | 22 | 0.21/NA/1.9 |
| C5 | Pea Protein, 0.9% Polyisocyanate, 1% BPEI,[6] 0.65% Emulsifier,[4] 1% Fragrance, 36% Core solvent,[2] 7.37% | 2.6 | 35 | Too viscous to test. |
| 16 | Pea Protein, 0.9% Polyisocyanate, 1% Emulsifier,[7] Fragrance, 36% Core solvent,[2] 7.37% | >5 | 21 | 0.75/NA/4.5 |
| 17 | Pea Protein, 0.9% Polyisocyanate, 1% Guanidine, 0.65% Emulsifier,[7] Fragrance, 36% Core solvent,[2] 7.37% | 0.7 | 28 | 0.75/NA/4.3 |
| C6 | Pea Protein, 0.9% Polyisocyanate, 1% HMDA,[5] 1.3% Emulsifier,[7] 1% Fragrance, 36% Core solvent,[2] 7.37% | >5 | 31 | Free oil is too high to test. |
| C7 | Pea Protein, 0.9% Polyisocyanate, 1% BPEI,[6] 0.65% Emulsifier,[7] 1% Fragrance, 36% Core solvent,[2] 7.37% | 2.6 | 35 | Free oil is too high to test. Too viscous to test. |
| 18 | Pea Protein, 0.9% Polyisocyanate, 1% Emulsifier,[8] 1.5% Fragrance, 36% Core solvent,[2] 7.37% | >5 | 21 | 3078[9] |
| 19 | Pea Protein, 0.9% Polyisocyanate, 1% Guanidine, 0.65% Emulsifier,[8] 1.5% Fragrance, 36% Core solvent,[2] 7.37% | 0.3 | 43 | 3423[9] |
| C8 | Pea Protein, 0.9% Polyisocyanate, 1% HMDA,[5] 1.3% Emulsifier,[8] 1.5% Fragrance, 36% Core solvent,[2] 7.37% | >5 | 25 | Free oil is too high to test. |
| C9[10] | Pea Protein, 0.9% Polyisocyanate, 1% BPEI,[6] 0.65% Emulsifier,[8] 1.5% Fragrance, 36% Core solvent,[2] 7.37% | NA | NA | NA |

TABLE 11-continued

| Example | Components wt %[1] | Free oil % | Particle size μm | Fragrance intensity Pre-rub/toss/post-rub |
|---|---|---|---|---|
| 20 | Pea Protein, 1.84% Polyisocyanate, 1% Guanidine, 1.3% Emulsifier,[8] 1.5% Fragrance, 36% Core solvent,[2] 7.37% | 2.5 | 88 | 9/10.4/11.9 |

[1]By weight of the microcapsule composition.
[2]Caprylic/capric triglyceride, commercially available as NEOBEE ® oil M-5.
[3]0.1% CMC/0.5% Flexan (II).
[4]0.5% PVP/0.5% PQ11.
[5]HMDA.
[6]BPEI.
[7]0.5% PVP/0.5% Morwet.
[8]1% PGU/0.5% Flexan (II).
[9]Post-rub headspace GC reading.
[9]Failed. No microcapsule was formed.

Example 21

Microcapsule Composition 21 was prepared using a brown rice protein. An oil phase was first prepared by mixing 40 g of a model fragrance and 10 g of caprylic/capric triglyceride (NEOBEE® oil M-5), and an aliphatic polyisocyanate (0.7 g, a polyisocyanate based on hexamethylene diisocyanate (HDI) commercially available under Desmodur® N100A, Bayer, Leverkusen, Germany). In a separate beaker, an aqueous solution was obtained by mixing an aqueous dispersion (34.33 g) containing 10% brown rice protein (denatured by heating the solution at 80° C. for 1 hour, commercially available as Oryzatein® Silk 90 from Axiom Foods, Inc., Los Angeles, California), an aqueous solution (5.72 g) of 10% OSA-modified starch (commercially available as Capsul® 6330 from Ingredion Inc., Bridgewater, New Jersey), an aqueous solution (5.80 g) of a 10% sodium salt of polystyrene sulfonate (a capsule formation aid, commercially available under the trade name of Flexan® II, AkzoNobel Surface Chemistry, Ossining, NY), an aqueous solution (0.12 g) of 20% DABCO crystalline (a catalyst, 1,4-Diazabicyclo[2.2.2]octane, Evonik, Essen, Germany), and water (13.9 g). The oil phase was then emulsified into the aqueous phase to form an oil-in-water emulsion under shearing at 9600 rpm for three minutes.

After the oil-in-water emulsion was stirred at 25° C. for 0.5 hours, 3.81 g of 30% tannic acid aqueous solution (Tana®-01, Ajinomoto, Japan) were added under constant mixing. The mixture was cured at room temperature for 1 hour and then 80° C. for 4 hours. The encapsulation efficiency is 99.9%.

Example 22

Microcapsule composition 22 was prepared following the same procedure as Example 21 except that an oil phase contained 45.78 g of a model fragrance and 11.14 g of caprylic/capric triglyceride (NEOBEE® oil M-5), and 0.7 g of an aliphatic polyisocyanate (Desmodur® N100A).

Microcapsule composition 22 was added to a fabric conditioner base at a level of 0.6% neat oil equivalence for evaluation. The fragrance intensity had a score of 7.1 at the pre-rub stage, 8.6 after tossed for 5 times, and 12.2 at the post-rub stage.

Example 23

Microcapsule composition 23 was prepared following the same procedure as Example 21 except that an oil phase contained 51.5 of a model fragrance and 12.46 g of caprylic/capric triglyceride (NEOBEE® oil M-5), and 0.7 g of an aliphatic polyisocyanate (Desmodur® N100A).

Example 24

Microcapsule composition 24 was prepared following the same procedure as Example 22 except that a pea protein (commercially available from Roquette, Lestrem, France) was used instead of the brown rice protein.

Example 25

Microcapsule composition 25 was prepared following the same procedure as Example 22 except that a potato protein (commercially available from Roquette, Lestrem, France) was used instead of the brown rice protein.

Example 26

Microcapsule composition 26 was prepared following the same procedure as Example 22 except that a whey protein (commercially available from Roquette, Lestrem, France) was used instead of the brown rice protein.

Example 27

Microcapsule composition 27 was prepared following the same procedure as Example 22 except that a white rice protein (commercially available from Roquette, Lestrem, France) was used instead of the brown rice protein.

Chitosan Coating

To improve deposition of the encapsulated fragrance, any microcapsules of this invention can be coated with chitosan as follows. A 3% chitosan (extracted from fungal) aqueous solution was prepared by dissolving chitosan in water together with 1% of acetic acid. A microcapsule composition was mixed with a diluted sulfuric acid solution until the pH reached 2. The chitosan solution was added to the acidified microcapsule composition so that the chitosan was present at a level of 2%. The resultant microcapsule composition had a pH of 2 and was heated to a temperature of 60° C. and kept at that temperature for 4 hours to obtain a microcapsule composition with a chitosan coating on the microcapsule.

The chitosan coated microcapsule composition can be further mixed with 0.25 wt % of the copolymer of acrylamide and acrylamidopropyltrimonium chloride (ACM-APTAC, as a deposition aid) or the copolymer of acrylamide and methacrylamidopropyl-trimonium chloride (ACM-MAPTAC, as a deposition aid) to obtain microcapsule compositions with a deposition aid.

The chitosan coated microcapsule compositions and the microcapsule composition with deposition aids showed a higher fragrance intensity in a hair conditioner evaluation as compared to microcapsule compositions without chitosan, ACM-APTAC, or ACM-MAPTAC.

Biodegradability

Biodegradability testing is carried out according to protocol OECD 310. An aliquot of microcapsule slurry is placed into Biological Oxygen Demand (BOD) bottles in water containing a microbial inoculum. The bottles are checked for carbon dioxide evolution at a regular interval for 60 days. Intermittent points can also be taken since an asymptotic value may be reached much sooner than 60 days. The percent degradation is analyzed against the positive control starch.

Consumer Product Examples

Microcapsule compositions of this invention can be added to various consumer products. Non-limiting examples are shown in Table 12 below.

TABLE 12

| | |
|---|---|
| Fabric Softener | Antiperspirant (AP) roll-on product |
| Microcapsule Composition, 0.1-2% NOE[2] | Microcapsule Composition, 0.1-2% NOE |
| Quat surfactant (active), 1-20% | Anionic surfactant, 1-3% |
| Stabilizer, <1% | Aluminum chlorohydrate, 10-20%, |
| pH buffer, <1% | Silica, less than 1% |
| Salt, <1% | Helianthus annuus, 1-2% |
| Preservative, <0.1% | Water, q.s. to 100% |
| Antifoam, <0.1 | |
| Water, q.s. to 100% | |
| Shampoo | Hair conditioner |
| Microcapsule Composition, 0.1-2% NOE | Microcapsule Composition, 0.1-2% NOE |
| Sodium lauryl ether sulphate, 12% | Fatty alcohol, 4% |
| Cocamidopropyl betaine, 1.6% | Behentrimonium chloride, 0.7% |
| Non-ionic guar, 0.2% | Terminal amino silicones, 1% |
| Silicone, 2-3% | Silicone, 2.5% |
| Preservative, 0.5% | Preservative, 0.5% |
| Water, q.s. to 100% | Water, q.s. to 100% |
| Powder detergent Example 1 | Powder detergent Example 2 |
| Microcapsule Composition, 0.1-2% NOE | Microcapsule Composition, 0.1-2% NOE |
| Sodium Carbonate, 81.9% | Sodium alkl benzene sulphonate, 7.6% |
| Ethoxylated $C_{12}$-$C_{15}$ alcohol sulfate salt, 4.3% | Nonionic surfactant, 9.8% |
| $C_{12}$-$C_{15}$ alcohol ethoxylate, 2.4% | Soap, 1.7% |
| Sodium Sulfate, 1.5% | sodium aluminosilicate (zeolite), 27% |
| Sodium bicarbonate, 1.3% | Sodium Carbonate, 13% |
| Sodium polyacrylate, 0.7% | Alkaline sodium silicate (1:3.3), 0.5% |
| Sodium Carboxymethylcellulose, 0.1% | CP5-polymer ex BASF, 4% |
| Optical Brightener, 0.2% | Sodium Carboxymethylcellulose (SCMC), 0.6% |
| Polyvinyl Alcohol, 0.1% | Water, 11% |
| Water, 7.4% | Minors, 1.5% |
| | Dry Additives |
| | Sodium perborate monohydrate (PBM), 14% |
| | Enzyme, 1.1% |
| | TAED granules (83%), 7.4% |
| | Ethylene diamine tetramethylene phosphonate (EDTMP), 0.4% |
| | anti-foam granules, 0.4% |
| Powder detergent Example 3 | Roll on deodorant |
| Microcapsule Composition, 0.1-2% NOE | Microcapsule Composition, 0.1-2% NOE |
| Zeolite, 36.6-45.9% | Aluminum Chlorohydrate 50% Solution, 30-34% |
| Sodium carbonate, 13.3-16.6% | Steareth-20, 1.3-1.9% |
| Soap, 0-0.7% | Steareth-2, 5-5.6% |
| Sodium sulphate, 0-2% | Silica, 0.5-1.1% |
| Sodium Carboxymethylcellulose (SCMC), 0-0.9% | Preservative, 0.7-1.3% |
| Fluorescer, 0-0.7% | |
| Sodium alkyl benzene sulphonate, 0-23.3% | |
| Primary Alkyl sulphate, 0-23.1% | |
| Nonionic 7 EO surfactant, 0-4.1% | |
| Nonionic 3 EO surfactant, 0-7% | |
| CP5 co-polymer ex BASF, 1-3% | |
| Alkaline Sodium silicate, 0-4% | |
| Water, 11.5-15.8% | |
| Liquid detergent | |
| Microcapsule Composition, 0.1-2% NOE | |
| A non-soap surfactant (anionic or nonionic) with a range of 15 wt. % to 45 wt. %, preferably 32 wt. % to 35 wt. % | |
| Propylene glycol, 0.5-50%, preferably 10-20% | |
| One or more soil release polymer (SRP) that can be between 0.01% and 10%, preferably 0.9% and 2.5%, | |
| Water, 5-35%, preferably 15-25% | |

[1]All component percentages are shown by weight of the consumer product.
[2]NOE is the neat fragrance oil equivalence which equals to the weight percentage of the fragrance oil in the consumer product.

Other Embodiments

All of the features disclosed in this specification may be combined in any combination. Each feature disclosed in this specification may be replaced by an alternative feature serving the same, equivalent, or similar purpose.

To achieve the purpose of encapsulating an active material, one skilled in the art can design and prepare a capsule composition by using different encapsulating polymers, coatings, and capsule formation aids, varying the concentrations of wall-forming materials or catalysts to achieve desirable release profiles in a consumable product. Further, the ratios among the wall forming materials, capsule forming aids, adjuvents, core modifiers, active materials, and catalysts can also be determined by a skilled artisan through known assays.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A microcapsule composition comprising microcapsules that contain a microcapsule core and a microcapsule wall encapsulating the microcapsule core, wherein the microcapsule core contains an active material and the microcapsule wall is formed of a polymeric network comprising a polyisocyanate and a cross-linker consisting of (i) whey or a plant storage protein and (ii) tannic acid, wherein the weight ratio of the protein to polyisocyanate is in the range of 1:1 to 10:1, and the microcapsules contain 50% to 90% of the protein by weight of the microcapsule wall.

2. The microcapsule composition of claim 1, wherein the plant storage protein is pea protein.

3. The microcapsule composition of claim 1, wherein the whey or plant storage protein is partially or completely denatured prior to formation of the polymeric network.

4. The microcapsule composition of claim 3, wherein at least 60% by weight of the whey or plant storage protein is denatured prior to formation of the polymeric network.

5. The microcapsule composition of claim 3, wherein the whey or plant storage protein is denatured with a guanidine salt.

6. The microcapsule composition of claim 3, wherein the whey or plant storage protein is denatured with guanidine carbonate.

7. A consumer product comprising the microcapsule composition of claim 1.

8. A method of preparing the microcapsule composition of claim 1, comprising the steps of:
    (a) emulsifying an oil phase comprising a polyisocyanate and an active material with an aqueous phase comprising a whey or plant storage protein thereby forming an oil-in-water emulsion;
    (b) adding tannic acid to the oil-in-water emulsion; and
    (c) applying conditions sufficient to induce formation of a polymeric network comprising the polyisocyanate, whey or plant storage protein and tannic acid, thereby forming the microcapsule composition comprising microcapsules that contains a microcapsule core and a microcapsule wall encapsulating the microcapsule core;
    wherein the microcapsule core contains the active material and the microcapsule wall is formed of the polymeric network comprising the polyisocyanate, whey or plant storage protein and tannic acid; and
    wherein the weight ratio of the protein to polyisocyanate is in the range of 1:1 to 10:1, and the microcapsules contain 50% to 90% of the protein by weight of the microcapsule wall.

9. The method of claim 8, wherein the plant storage protein is pea protein.

10. The method of claim 8, wherein the whey or plant storage protein is partially or completely denatured prior to step (a).

11. The method of claim 10, wherein at least 60% by weight of the whey or plant storage protein is denatured.

12. The method of claim 10, wherein the whey or plant storage protein is denatured with a guanidine salt.

13. The method of claim 10, wherein the whey or plant storage protein is denatured with guanidine carbonate.

* * * * *